United States Patent [19]

Han

[11] Patent Number: 5,326,863

[45] Date of Patent: Jul. 5, 1994

[54] AZETIDIN-2-ONE DERIVATIVES AS SERINE PROTEASE INHIBITORS

[75] Inventor: William T. Han, Cheshire, Conn.

[73] Assignee: Bristol-Myers Squibb Company, New York, N.Y.

[21] Appl. No.: 96,321

[22] Filed: Jul. 23, 1993

Related U.S. Application Data

[62] Division of Ser. No. 957,233, Oct. 6, 1992, Pat. No. 5,250,677, which is a division of Ser. No. 833,876, Feb. 11, 1992, Pat. No. 5,175,283, which is a division of Ser. No. 696,641, May 7, 1991, Pat. No. 5,110,812, which is a division of Ser. No. 533,270, Jun. 4, 1990, Pat. No. 5,037,819.

[51] Int. Cl.$^5$ .................. C07D 205/09; C07D 205/08; A61K 31/395; C07B 53/00
[52] U.S. Cl. .................................................... 540/200
[58] Field of Search ........................................ 540/200

[56] References Cited

U.S. PATENT DOCUMENTS

| | | | |
|---|---|---|---|
| 4,623,645 | 11/1986 | Doherty et al. | 540/228 |
| 4,637,999 | 1/1987 | Doherty et al. | 540/228 |
| 4,680,391 | 7/1987 | Firestone et al. | 540/200 |
| 4,699,904 | 10/1987 | Doherty et al. | 540/228 |
| 4,717,722 | 1/1988 | Doherty et al. | 540/302 |
| 4,845,088 | 7/1989 | Doherty et al. | 540/302 |

FOREIGN PATENT DOCUMENTS

| | | |
|---|---|---|
| 0264231 | 4/1988 | European Pat. Off. . |
| 0264232 | 4/1988 | European Pat. Off. . |
| 62-87562 | 4/1987 | Japan . |

OTHER PUBLICATIONS

Doherty, et al., Cephalosporin Antibiotics Can Be Mmodified to Inhibit Human Leukecyte Elastase, *Nature*, 322, 10, p. 192 (1986).

Gianfranco, C., et al. Stereocontrolled Total Synthesis of Chiral Building Block (3S,4R)-3-[(R)-1-Hydroxyethyl)-4-Acetyloxy-Azetidin-2-One; A Useful Synthon for the Synthesis of (+)-Thienamycin, Carbapenems and Penems. *Tetrahedron Letters*, 26, No. 7, pp. 937-940, (1985).

*Primary Examiner*—Mark L. Berch
*Attorney, Agent, or Firm*—William T. Han

[57] ABSTRACT

The present invention relates to new 3-guanidinoalkyl-2-azetidinones of the formula wherein:
U and W can be the same or different and are selected from the group consisting of hydrogen and an amino protecting group;
n is 1 to 3;
X is a member selected from the group consisting of hydrogen, trialkylsilyl, arylsulfonyl, amino substituted arylsulfonyl, alkylsulfonyl, arylaminocarbonyl, alkylcarbonyl and arylcarbonyl; and
Y is a member selected from the group consisting of hydrogen, arylalkenyl, arylalkyl, formyl, carboxy, alkoxycarbonyl, acyloxy, arylthio, arylsulfinyl, arylsulfonyl, alkylthio, alkylsulfinyl, alkylsulfonyl, arylaminocarbonyl, the radical $$-\overset{O}{\underset{\|}{C}}-NH-CH_2\overset{O}{\underset{\|}{C}}-OR$$

in which R is hydrogen, alkyl or arylalkyl, and the radical in which m is 1 to 3 and R' is hydrogen or —CO$_2$R" wherein R" is hydrogen, alkyl or arylalkyl.

The novel azetidinones of the present invention exhibit anti-thrombin and anti-trypsin activities and are thus useful in controlling blood coagulation and treating pancreatitis.

2 Claims, No Drawings

AZETIDIN-2-ONE DERIVATIVES AS SERINE PROTEASE INHIBITORS

CROSS REFERENCE TO RELATED APPLICATION

This application is a divisional application of U.S. Ser. No. 07/957,233 filed Oct. 6, 1992, U.S. Pat. No. 5,250,677; which is a divisional of U.S. Ser. No. 07/833,876 filed Feb. 11, 1992, now U.S. Pat. No. 5,175,283; which is a divisional of U.S. Ser. No. 07/696,641 filed on May 7, 1991, now U.S. Pat. No. 5,110,812; which is a divisional of U.S. Ser. No. 07/533,270 filed Jun. 4, 1990, now U.S. Pat. No. 5,037,819.

BACKGROUND OF THE INVENTION

1. Field of the Invention

This invention relates to novel 3-guanidinoalkyl-2-azetidinones useful for anti-thrombin and anti-trypsin activity.

2. Description of Related Art

The traditional use of compounds containing beta-lactam structures has been for antibacterial activities. However, certain beta-lactams have been identified as having activity against serine proteases. Compounds having activity against serine proteases could be used to treat certain degenerative conditions. For example, several patents, namely U.S. Pat Nos. 6,680,391 (issued Jul. 14, 1987), U.S. Pat. No. 4,623,645 (issued Nov. 18, 1986), and U.S. Pat. No. 4,637,999 (issued Jan. 20, 1987), disclose substituted azetidiones which are inhibitors of human leukocyte elastase (HLE), a serine protease. Such HLE inhibitors could be used to treat degenerative conditions such as arthritis and emphesyma.

Thrombin is another serine protease which cleaves fibrinogen to fibrin. Inhibitors of the enzyme could be useful for the control of blood coagulation. A number of synthetic inhibitors have been discovered. For a comprehensive review, see: Pharmakologie Synthetischem Thrombin Inhibitoren, J. Hamptmann and F. Markwardt, Berlin, 1986. Until recently, no synthetic thrombin inhibitor which contained azetidione nucleus was reported.

A recent article in Nature [J. B. Doherty, et al., Nature, 322, 192 (1982)] discloses the testing of certain cephalosporin sulfoxides for inhibiting a battery of serine proteases. Their ability to inhibit thrombin and trypsin was generally found to be much weaker than their ability to inhibit HLE.

More remote art of the present invention is found in European Patent Application Nos. 264,231 (published Apr. 20, 1988) and 264, 232 (published Apr. 20, 1988) and in Japanese Kokai No. 62-87562 (published Apr. 22, 1987) which disclose 2-azetidinone derivatives for blood platelet aggregation inhibitors.

This invention relates to novel 3-guanidinoalkyl-2-azetidinones as potent thrombin and trypsin inhibitors. None of the references discloses the instant 3-guanidinoalkyl-2-azetidinones as serine protease inhibitors.

SUMMARY OF THE INVENTION

The present invention relates to new 3-guanidinoalkyl-2-azetidinones of the formula

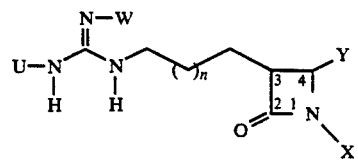

wherein:
U and W can be the same or different and are selected from the group consisting of hydrogen and an amino protecting group;
n is 1 to 3;
X is a member selected from the group consisting of hydrogen, trialkylsilyl, arylsulfonyl, amino substituted arylsulfonyl, alkylsulfonyl, arylaminocarbonyl, alkylcarbonyl and arylcarbonyl; and
Y is a member selected from the group consisting of hydrogen, arylalkenyl, arylalkyl, formyl, carboxy, alkoxycarbonyl, acyloxy, arylthio, arylsulfinyl, arylsulfonyl, alkylthio, alkylsulfinyl, alkylsulfonyl, arylaminocarbonyl, the radical

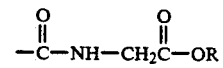

in which R is hydrogen, alkyl or arylalkyl, and the radical

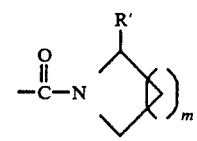

in which m is 1 to 3 and R' is hydrogen or —CO$_2$R" wherein R" is hydrogen, alkyl or arylalkyl.

The compounds are useful for anti-thrombin and anti-trypsin activities or as intermediates in the preparation of compounds having such utilities.

DETAILED DESCRIPTION OF THE INVENTION

This application relates to novel azetidinone derivatives which are potent inhibitors against serine proteases, in particular against thrombin and trypsin. More specifically, it relates to 3-guanidinoalkyl-2-azetidinones of the formula

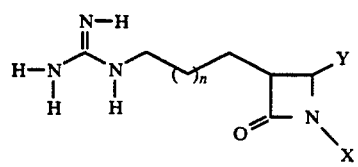

wherein:
n is 1 to 3;
X is a member selected from the group consisting of arylsulfonyl, amino substituted arylsulfonyl, alkylsulfonyl, arylaminocarbonyl, alkylcarbonyl and arylcarbonyl; and Y is a member selected from the group consisting of hydrogen, arylalkyl, carboxy, alkoxycarbonyl, acyloxy, arylsulfonyl, alkylthio, alkylsulfonyl, arylaminocarbonyl, the radical

in which R is hydrogen, alkyl or arylalkyl, and the radical

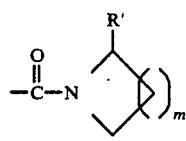

in which m is 1 to 3 and R' is hydrogen or —CO$_2$R'' wherein R'' is hydrogen, alkyl, or arylalkyl. In prefered Formula A compounds of the present invention, n has a value of 1 or 2, m is 2 or 3, R is hydrogen, and R' is carboxy or hydrogen.

In another aspect, this invention provides a method to control blood coagulation or to treat pancreatitis in an animal host which comprises administering to said host in need of such treatment a therapeutically effective amount of a compound of Formula A.

Also included within the scope of the invention are nontoxic pharmaceutically acceptable salts, physiologically hydrolyzable esters, or solvates of the compounds of Formula A. The nontoxic pharmaceutically acceptable salts of the compounds of Formula A include salts with mineral acids such as hydrochloric, hydrobromic, phosphoric and sulfuric, or with organic carboxylic acids or sulfonic acids such as acetic, trifluoroacetic, citric, maleic, oxalic, succinic, benzoic, tartaric, fumaric, mandelic, ascorbic, malic, methanesulfonic, p-touenesulfonic, and the like. Preparation of these acid additions salts is carried out by conventional techniques.

The invention also includes within its scope pharmaceutical compositions containing an effective thrombin or trypsin inhibiting amount of a compound of Formula A in combination with an inert pharmaceutically acceptable carrier or diluent. Such compositions may also contain other active agents and may be made up in any pharmaceutical form appropriate for the desired route of administration. Examples of such compositions include solid compositions for oral administration such as tablets, capsules, pills, powders and granules, liquid compositions such as solutions, suspensions, syrups or elixirs and preparations for parenteral administration such as sterile aqueous or non-aqueous solutions, suspensions or emulsions. They may also be manufactured in the form of sterile solid compositions which can be dissolved in sterile water, physiological saline or some other sterile injectable medium immediately before use.

Optimal dosages and regimens of the compound of Formula A, wherein n, X and Y are as previously defined, for a given mammalian host can be readily ascertained by those skilled in the art. It will, of course, be appreciated that the actual dose used will vary according to the particular composition formulated, the mode of application and the particular situs, host and condition being treated. Many factors that modify the action of the drug will be taken into account including age, weight, sex, diet, time of administration, route of administration, condition of the patient, drug combinations, reaction sensitivities and severity of the condition being treated. Administration can be carried out continuously or periodically within the maximum tolerated dose. Optimal application rates for a given set of conditions can be ascertained by those skilled in the art using conventional dosage determination tests in view of the above guidelines.

In another aspect, this application relates to a process for the preparation of the compounds of Formula A. Compounds of this invention can be prepared from common intermediates 3a' and 3b'

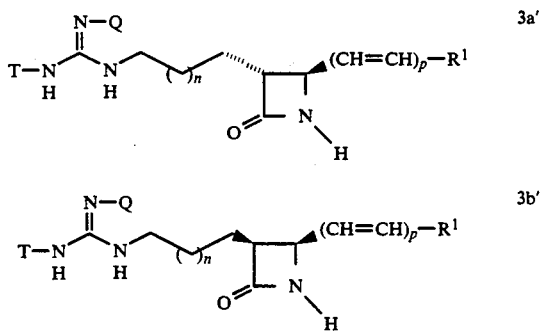

wherein p is 1 or 2; n is 1 to 3; R$^1$ is phenyl or alkyl substituted phenyl; Q and T can be the same or different amino protecting groups. For a range of amino protecting groups that can be used, see T. W. Greene, "Protective Groups in Organic Synthesis", 1981, John Wiley, New York, the disclosure of which is incorporated herein by reference. In the present invention, preferred protecting groups are phenylmethoxycarbonyl (Cbz) and t-butyloxycarbonyl groups. Compounds 3a' and 3b' can be prepared by a process which comprises the following steps or appropriate modifications thereof:

(a) reacting an isourea of Formula i with an amino acid of Formula ii to afford an acid of Formula iii

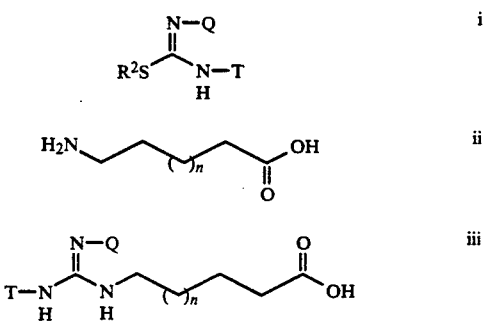

wherein R$^2$ refers to an alkyl group, preferably a primary alkyl group, and n, Q and T are as previously defined;

(b) esterifying a compound of Formula iii to an ester of Formula iv

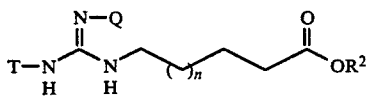

by activating the acid group in Formula iii with an activating agent such as carbonyldiimidazole and reacting the resultant imidazolide with an alcohol, preferably methanol, wherein $R^2$ refers to an alkyl group, preferably methyl group;

(c) forming a trianion of a compound of Formula iv by using a strong base such as lithium diisopropylamide, sodium hexamethyldisilizide, potassium hexamethyldisilizide, lithium hexamethyldisilizide, and the like, and reacting said trianion with a silylimine of Formula v to afford an azetidinone of Formula vi,

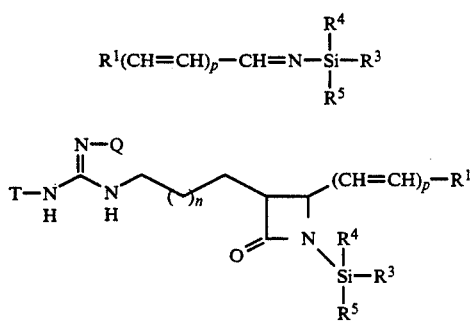

wherein $R^3$, $R^4$, and $R^5$ can independently be alkyl, phenyl, or alkyl substituted phenyl;

(d) hydrolyzing the nitrogen-silicon bond in a compound of Formula vi under acidic condition to afford a pair of stereoisomers of Formulas $3a'$ and $3b'$ in varying proportions which may be separated from each other and isolated by separation techniques well known in the art, such as by silica gel column chromatography.

As used herein, "alkyl" means a group containing from 1 to 4 straight or branched carbon atoms; "alkoxy" means an alkyl group attached to oxygen; "acyloxy" refers to an alkyl group attached to carbonyl; "aryl" means a phenyl or naphthyl group which may be unsubstituted or substituted with one or more groups such as amino, nitro, or alkyl; "amino" refers to an amino group unsubstituted or subtituted with one or two alkyl radicals; and "alkenyl" refers to a group containing 2 to 4 carbon atoms with 1 or 2 double bonds. Moreover, the invention embraces both E and Z forms which arise from double bond(s) in alkenyl groups.

It will be appreciated that one or both carbon atoms at positions 3 and 4 on the azetidinone core structure are chiral carbons, thus rendering a compound containing them to exist as optical isomers. It should be emphasized that the structures, as drawn in the specification, are not to be understood as representing specific enantiomers or tautomers (said tautomers arising from different positions of hydrogen atoms or a double bond in a guanidino moiety). The present invention intends to embrace all enantiomeric and tautomeric variations which are possible from the drawn structures. Further, depending upon the structural orientation of substituents attached to the 3 and 4 positions of the azetidinone, a compound may exist as either a cis or trans isomer. The present invention also intends to embrace both cis and trans isomers, unless otherwise specified.

DESCRIPTION OF SPECIFIC EMBODIMENTS

In compounds of the present invention having the general formula,

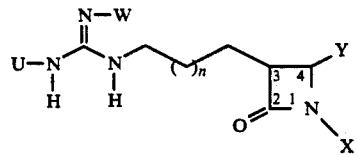

specific examples of the group X include:

hydrogen,
t-butyldimethylsilyl,
p-toluenesulfonyl,
acetyl,
(5-dimethylamino)-1-naphthalenesulfonyl,
methylsulfonyl,
phenylaminocarbonyl,
t-butylcarbonyl, and
phenylcarbonyl.

Specific examples of the group Y include:

hydrogen,
2-phenylethenyl,
2-phenylethyl,
formyl,
carboxy,
methoxycarbonyl,
acetyloxy,
phenylthio,
phenylsulfonyl,
ethylthio,
ethylsulfonyl,
1-piperidinocarbonyl,
4-methylbenzeneaminocarbonyl,
[2-[(phenylmethoxy)carbonyl]-1-pyrrolidinyl]carbonyl,
[[2-oxo-2-(phenylmethoxy)ethyl]amino]carbonyl,
(2-carboxy-1-pyrrolidinyl)carbonyl, and
[(2-hydroxy-2-oxoethyl)amino]carbonyl.

The reaction schemes and specific examples which follow illustrate the synthesis of representative compounds of the instant invention, and are not to be construed as limiting the invention in sphere or scope. The methods disclosed may be adopted to variations in order to produce compounds embraced by this invention but not specifically disclosed. Further, variations of the methods to produce the same compounds in somewhat different fashion will also be evident to one skilled in the art.

Referring to Scheme 1, the intermediate 1 is prepared by reacting N,N'-dicarbobenzyloxy-5-methylisothiourea with 5-aminovaleric acid. Compound 1 is esterified to form the corresponding methyl ester 2 which is cyclized by reaction with N-(trimethylsilyl)cinnamilyldenimine to form a mixture of isomers 3a and 3b. Isomers 3a and 3b are separated and then are individually converted to compounds 4a and 4b by reaction with t-butyldimethylsilyl chloride. Compounds 4a and 4b are individually ozonized to form aldehydes 5a and 5b which are treated with Jones reagent to form compounds 6a and 6b.

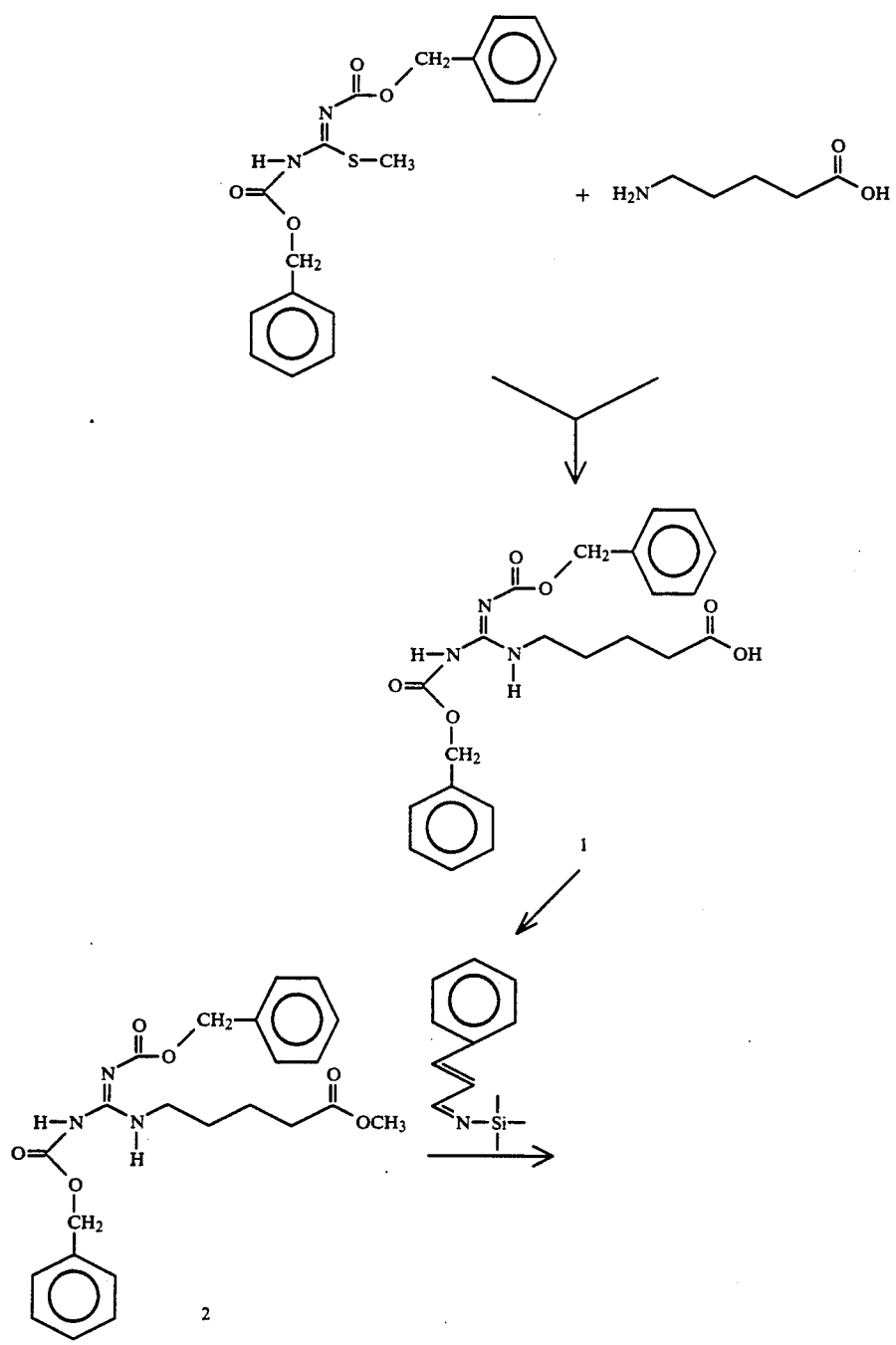

-continued
Scheme 1
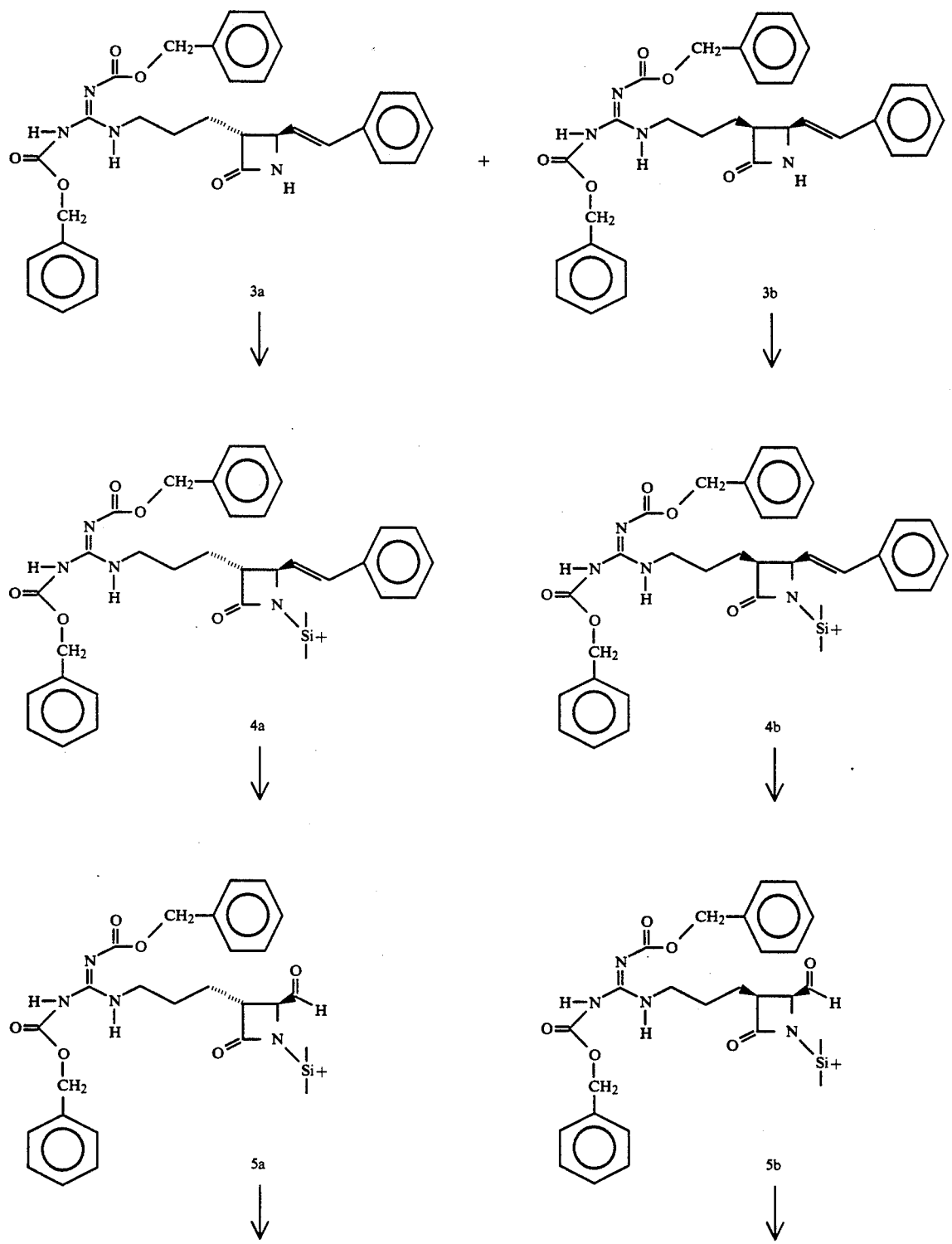

-continued
Scheme 1

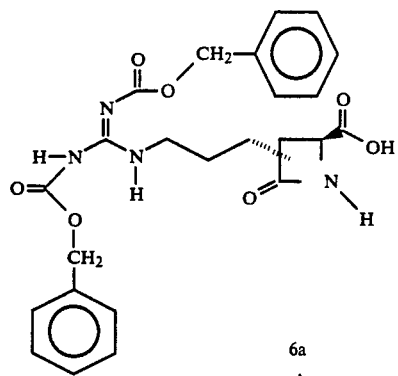

6a (To Scheme 2)

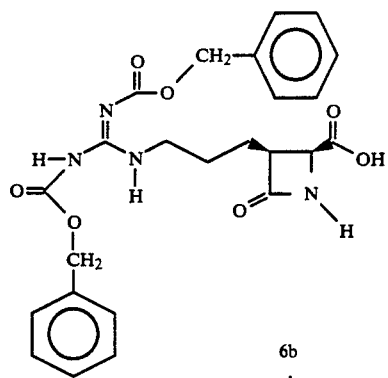

6b (To Scheme 11)

each of which is then catalytically hydrogenolyzed to remove the amino protecting groups, to yield compounds I, II, III, IV and V, respectively.

Referring to Scheme 2, compound 6a is esterified to give compound 7. Compound 7 is treated with various reagents as specified hereinafter to replace the proton at the 1-position to give compounds 8, 9, 10, 11 and 12, Scheme 2

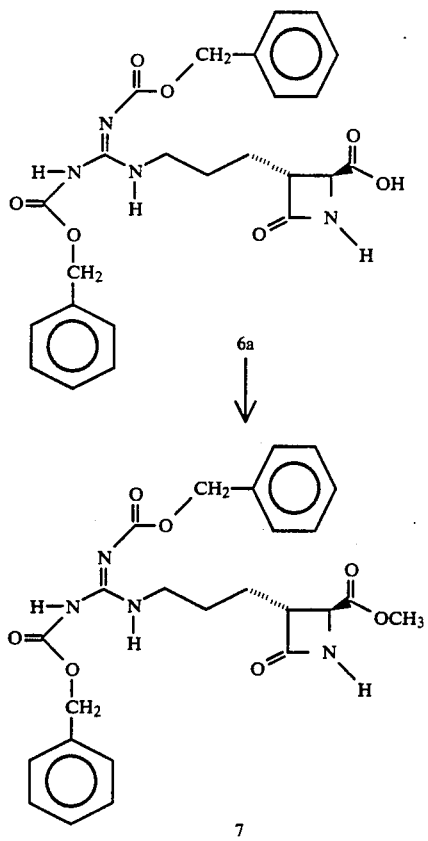

-continued
Scheme 2
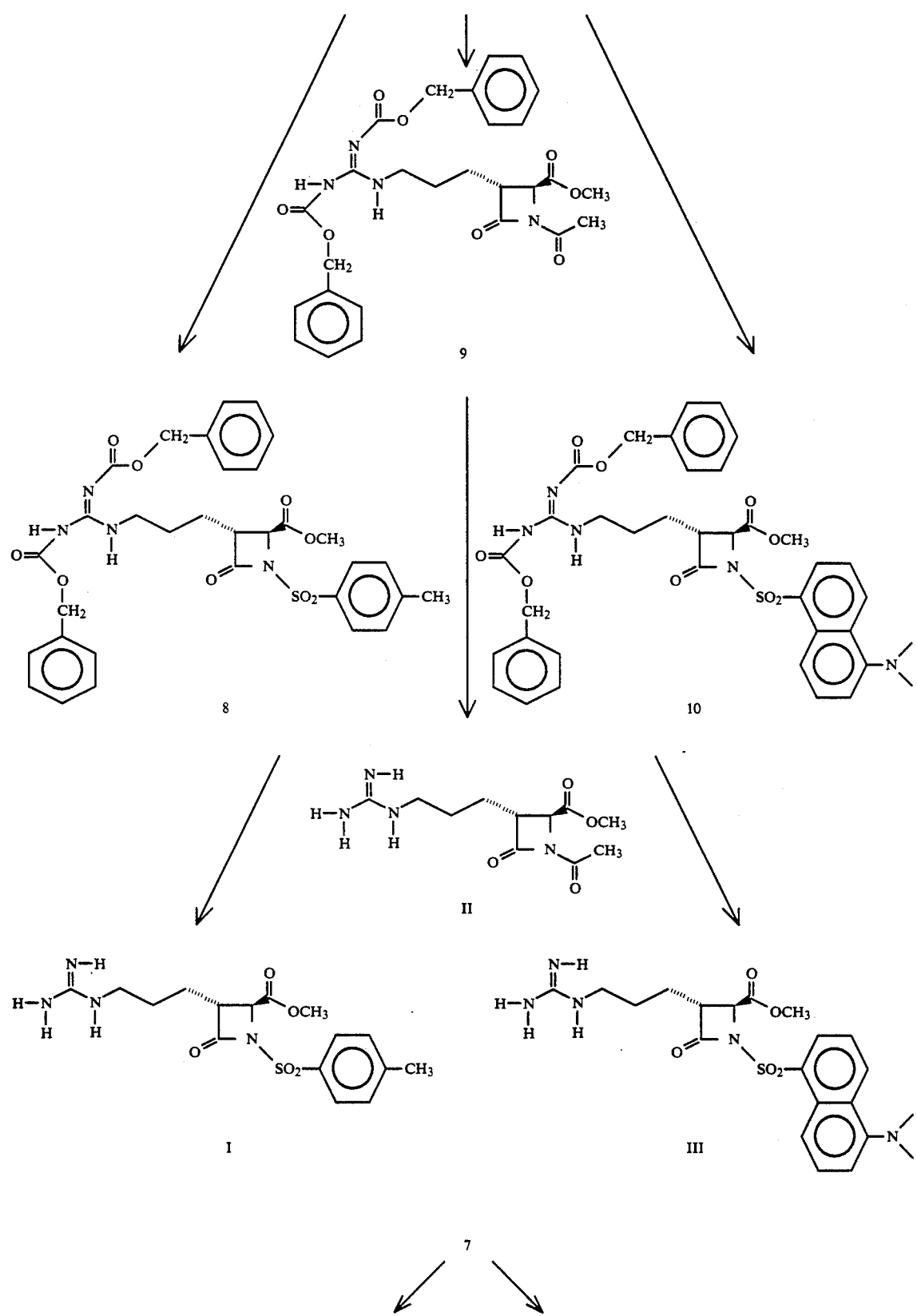

Scheme 2 -continued

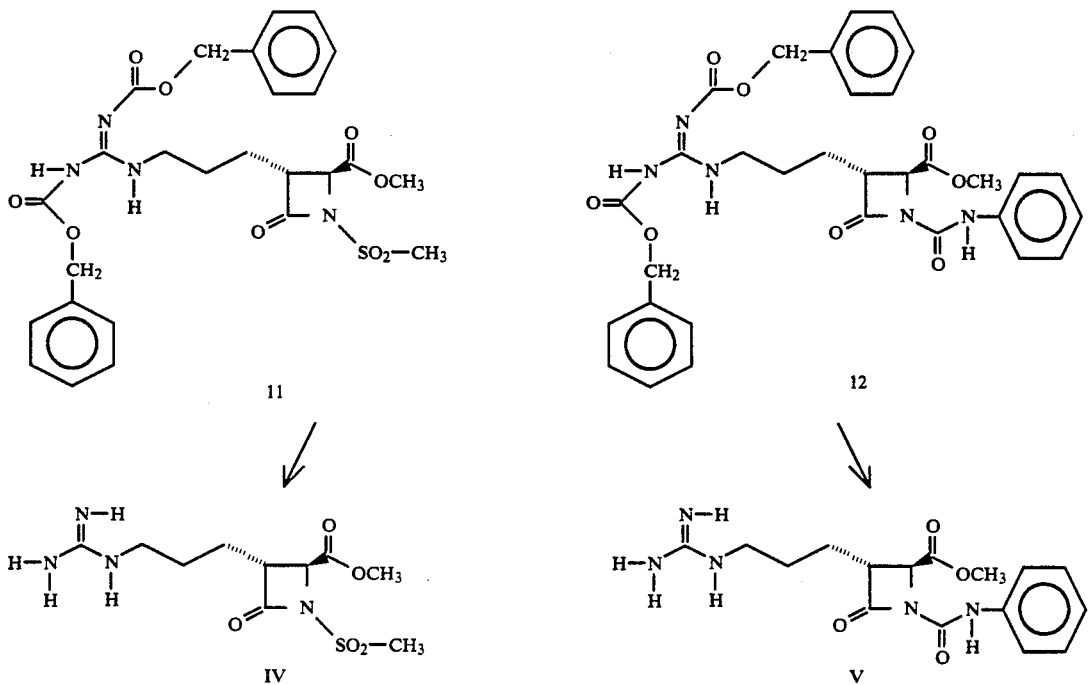

Referring to Scheme 3, compound 6a is reacted with lead tetraacetate to place an acetyloxy group on the 4-position to form compound 13. Compound 13 is reacted with sodium thiophenoxide to produce compound 14, which is reacted with acetyl chloride to yield compound 15. Compound 15 is oxidized to give compound 16, which is then catalytically hydrogenolyzed to remove the amino protecting groups to yield compound VI. Alternatively, compound 13 is reacted with sodium salt of ethanethiol to produce compound 17, which is then reacted with acetyl chloride to yield compound 18. Removal of the amino protecting groups by catalytic hydrogenolysis from compound 18 yields compound VII.

Scheme 3

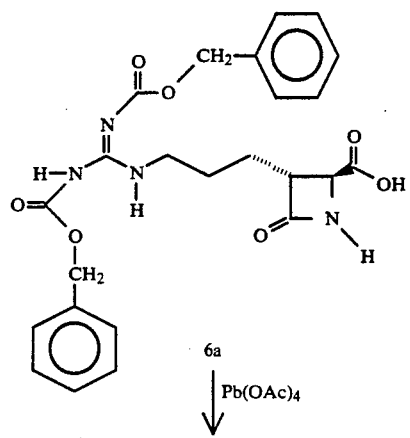

6a

↓ Pb(OAc)₄

-continued
Scheme 3
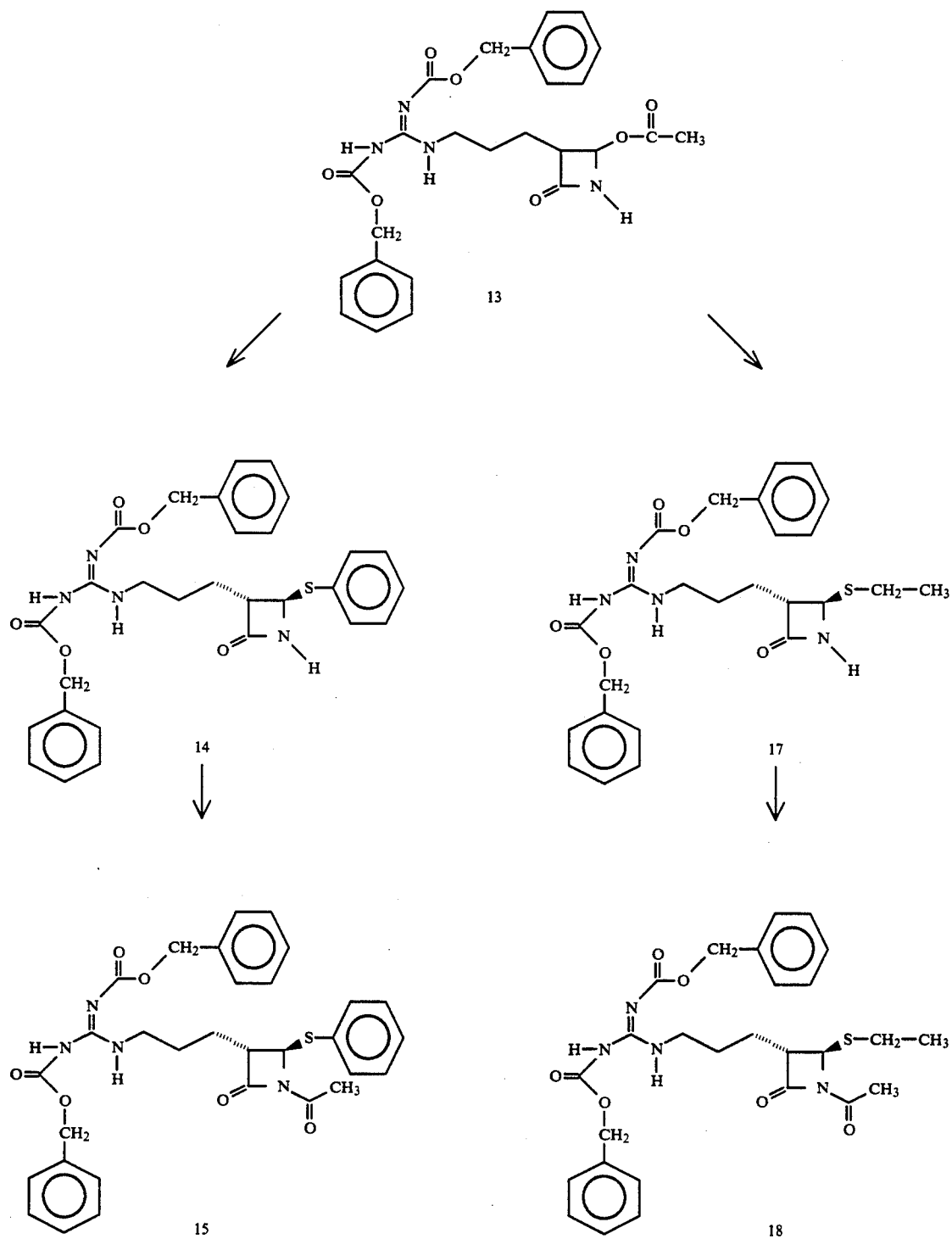

-continued
Scheme 3

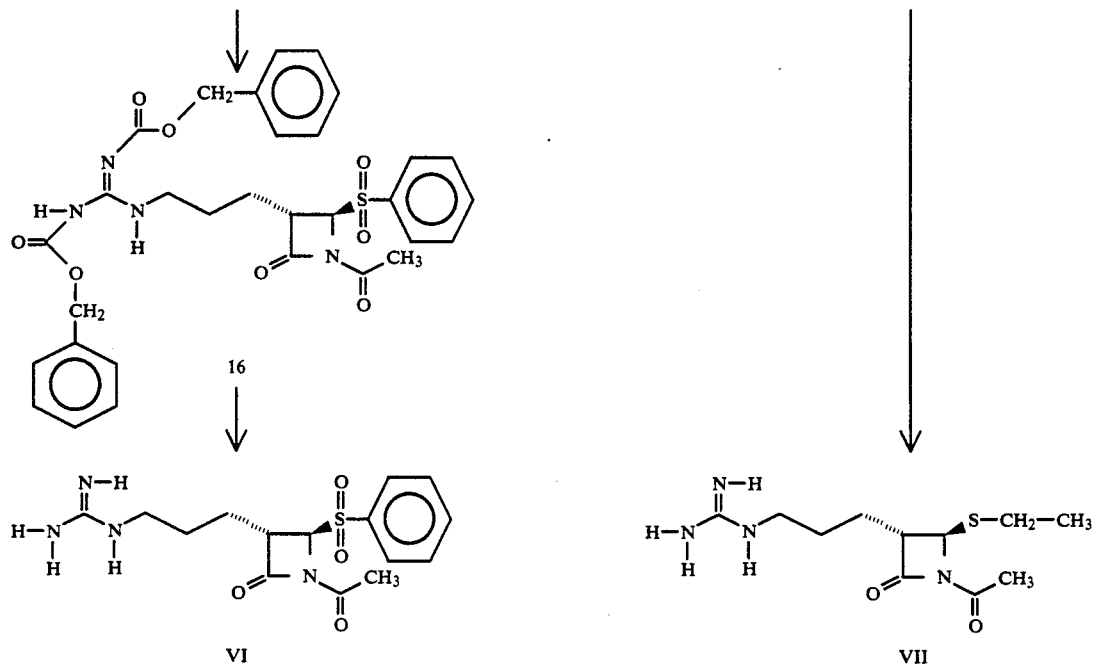

20 and 21, each of which is then catalytically hydrogenolyzed to remove the amino protecting groups to yield compounds VIII and IX, respectively.

Referring to Scheme 4, compound 17 is treated with Raney-Nickel to form compound 19. Compound 19 is treated with various reagents as described hereinafter to replace the proton at the 1-position to give compounds Scheme 4

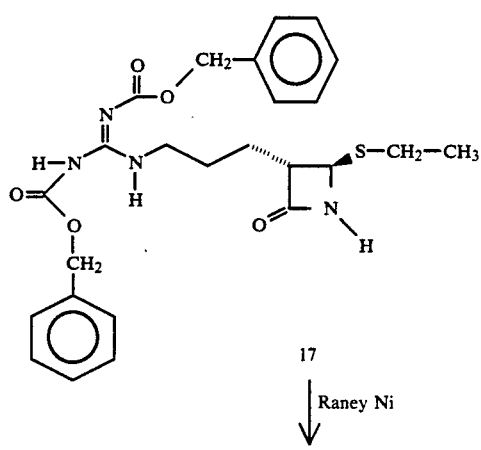

-continued
Scheme 4
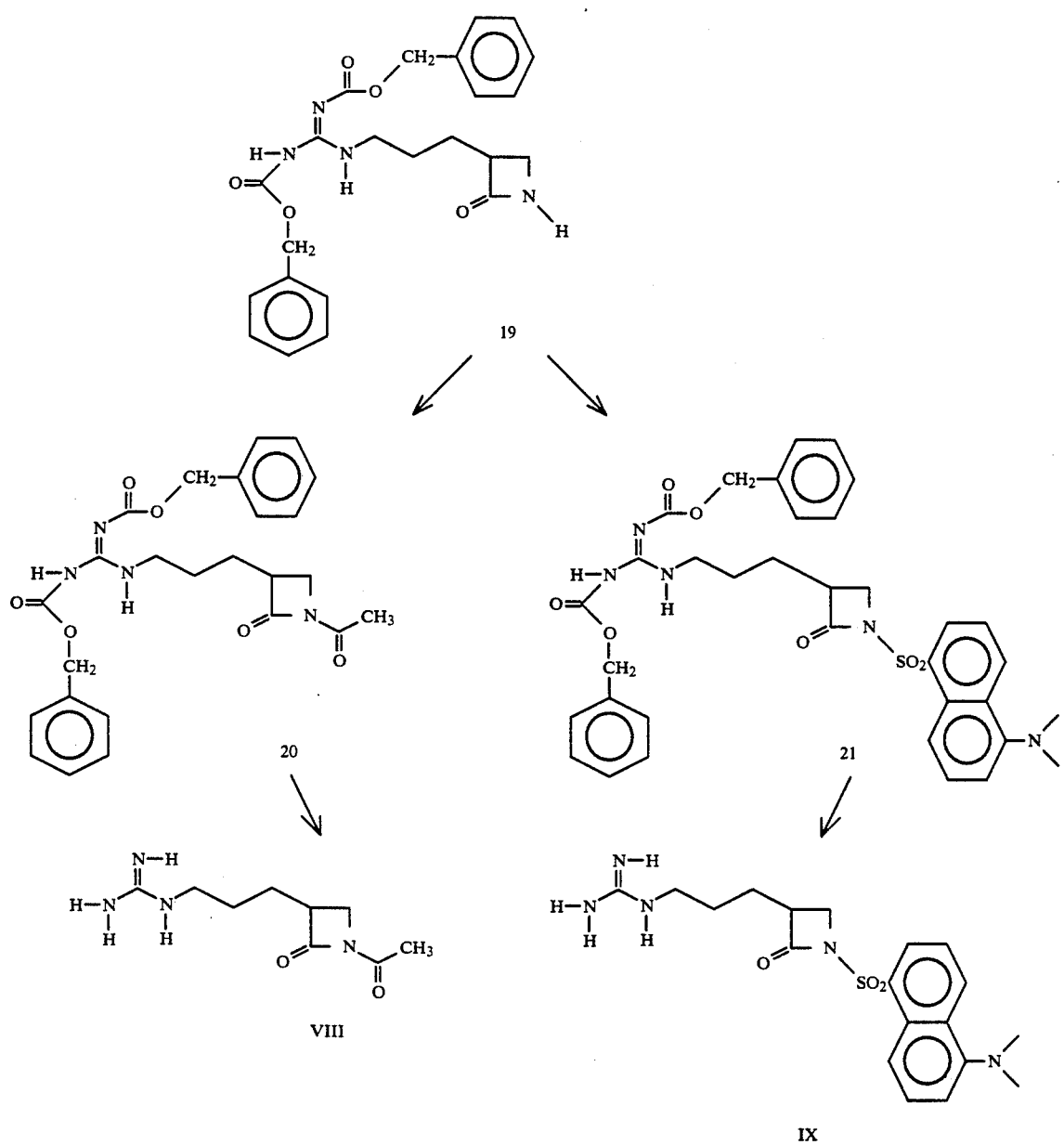
drogenolyzed to remove the amino protecting groups to yield compound X.
Referring to Scheme 5, compound 18 is oxidized to give compound 22 which is then catalytically hy- Scheme 5

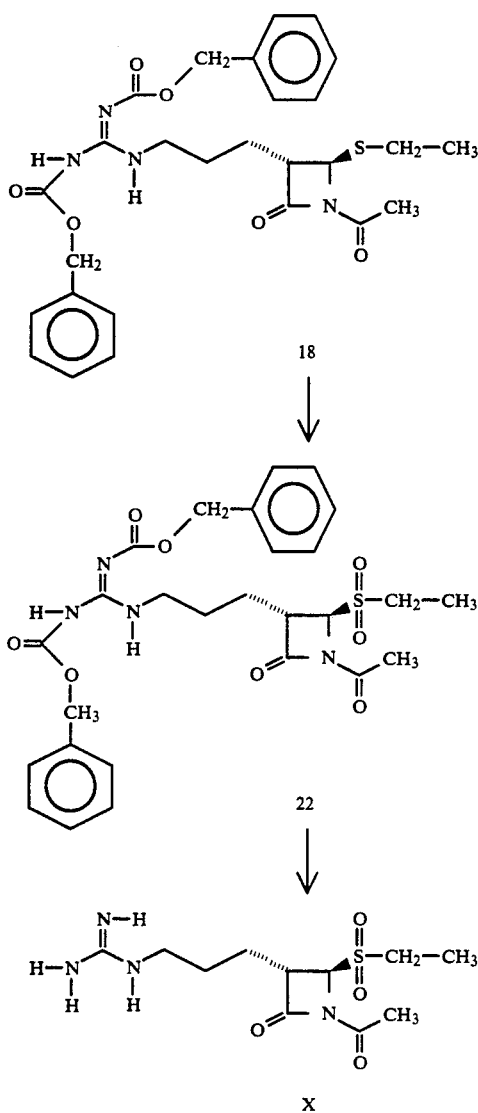

tecting groups to yield compounds XI, XII and XIII, respectively.

Referring to Scheme 6, compound 6a is reacted with piperidine to give compound 23. Compound 23 is treated with various reagents as specified hereinafter to replace the proton at the 1-position to give compounds 24, 25 and 26, each of which is then catalytically hydrogenolyzed with hydrogen to remove the amino pro- Scheme 6
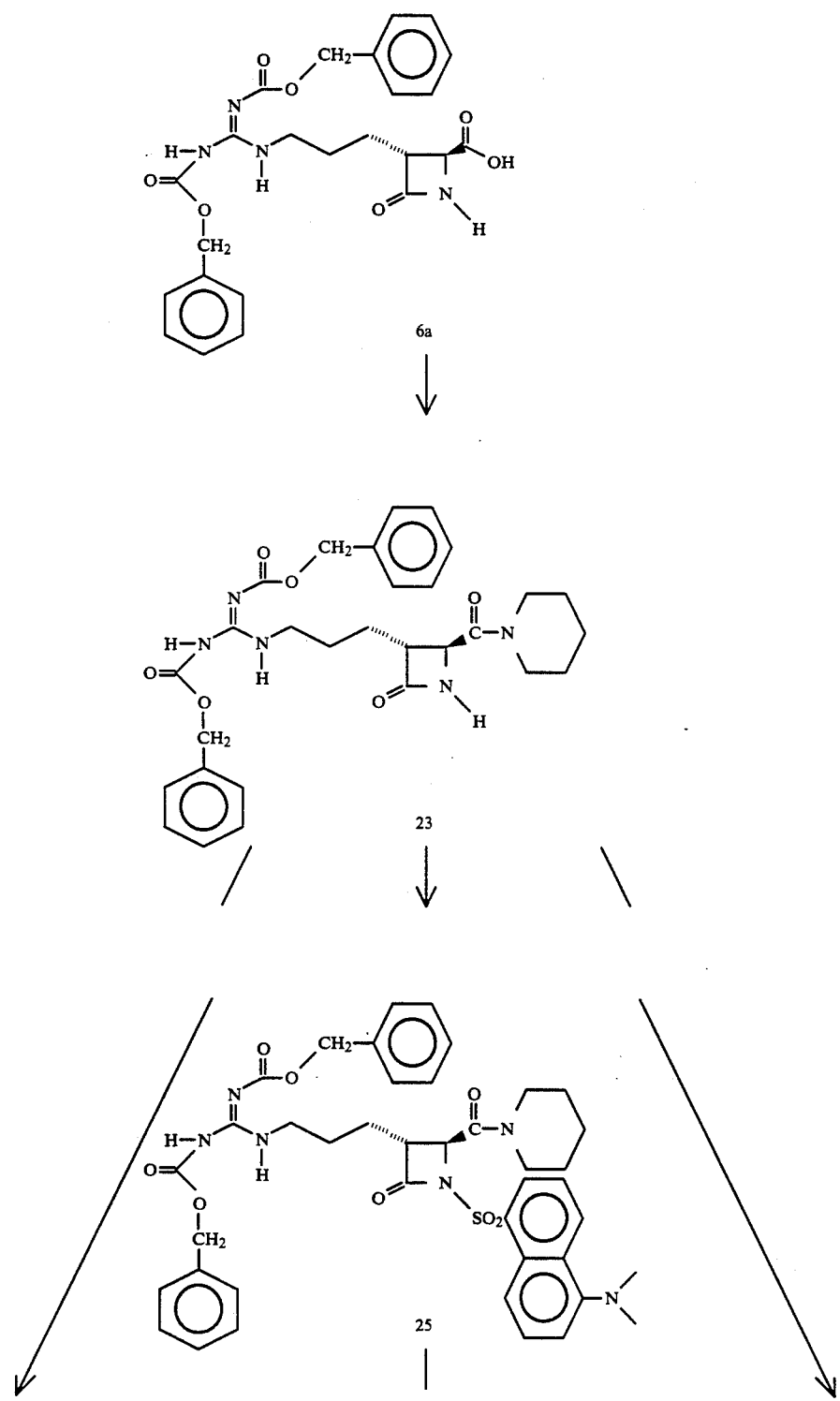

27 5,326,863 28

-continued
Scheme 6

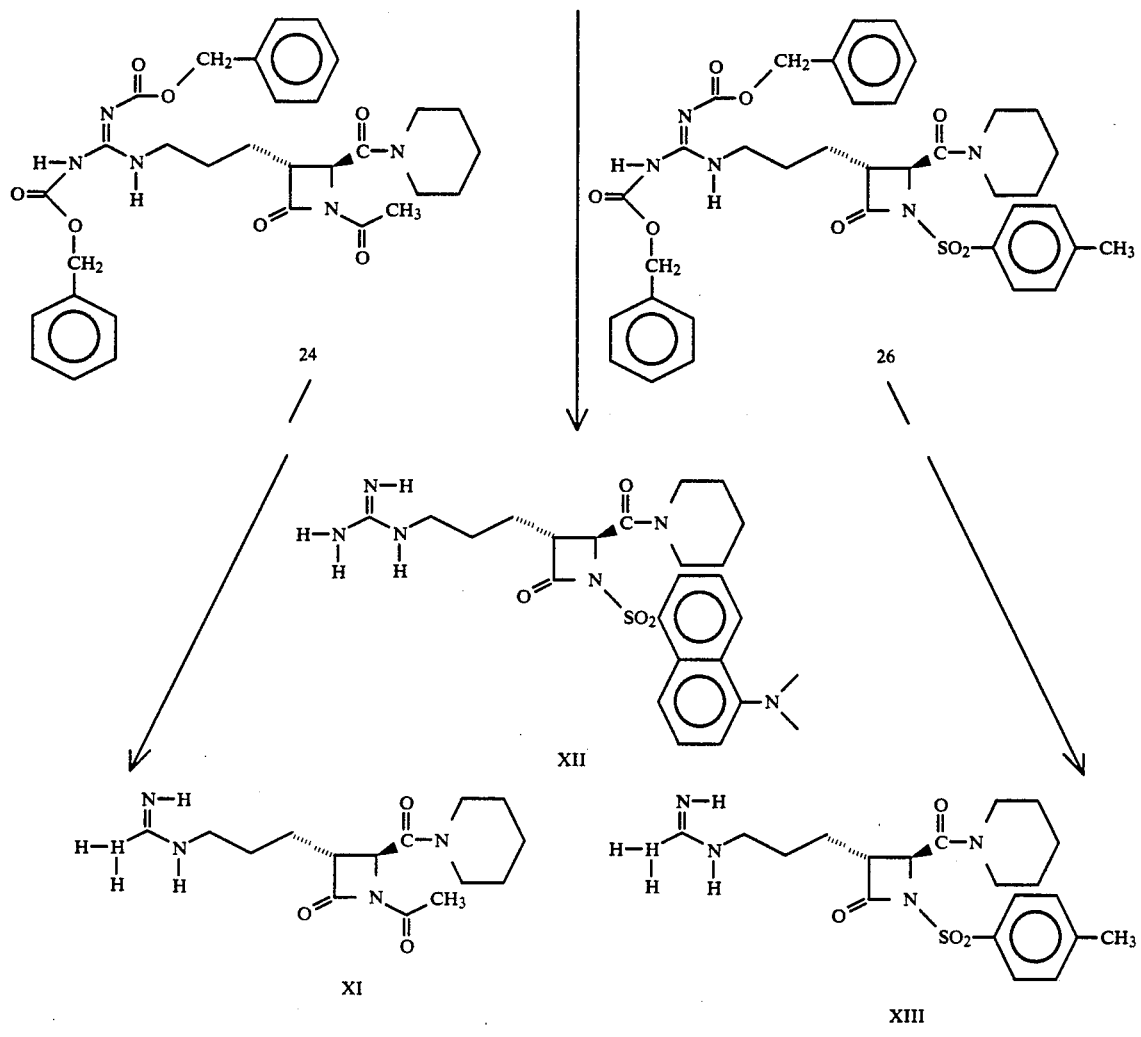

olysis to yield compound XIV. Compound 27 is also hydrogenated to yield compound XV. Compound 29 is also reacted with p-toluidene to form compound 30, which is catalytically hydrogenolyzed to remove the amino protecting groups to yield compound XVI.

Referring to Scheme 7, compound 3a is reacted with acetyl chloride to give compound 27, which is ozonized to form aldehyde 28. Aldehyde 28 is treated with Jones reagent to form compound 29 from which the amino protecting groups are removed by catalytic hydrogen- Scheme 7
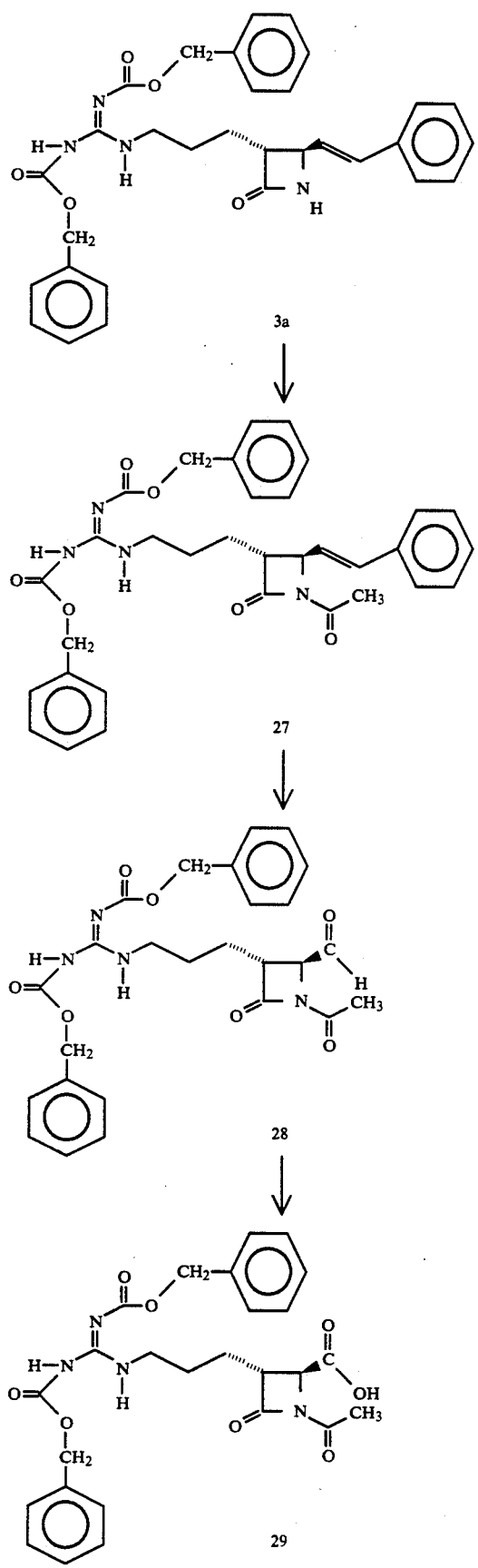

-continued
Scheme 7

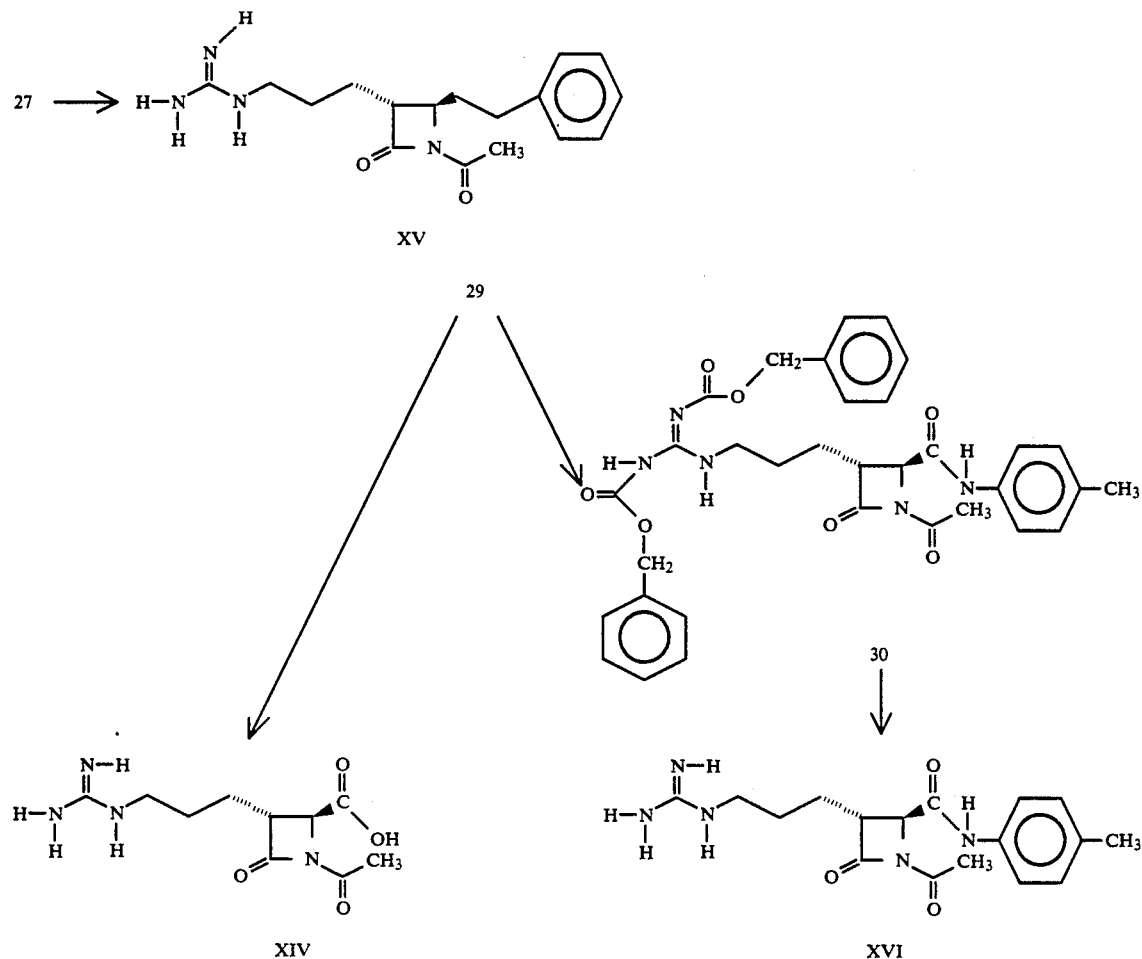

dimethylsilyl chloride. Compound 34 is ozonized to form aldehyde 35 which is treated with Jones reagent and subsequently esterified to form compound 36. Compound 36 is reacted with dansyl chloride to give compound 37 from which the amino protecting groups are removed by catalytic hydrogenolysis to yield compound XVII.

Referring to Scheme 8, the intermediate 31 is prepared by reacting N,N'-dicarbobenzyloxy-S-methylisothiourea with 6-aminocaproic acid. Compound 31 is esterified to form the corresponding methyl ester 32 which is cyclized by reaction with N-(trimethylsilyl)-benzaldimine to form compound 33. Compound 33 is converted to compound 34 by reaction with t-butyl- Scheme 8
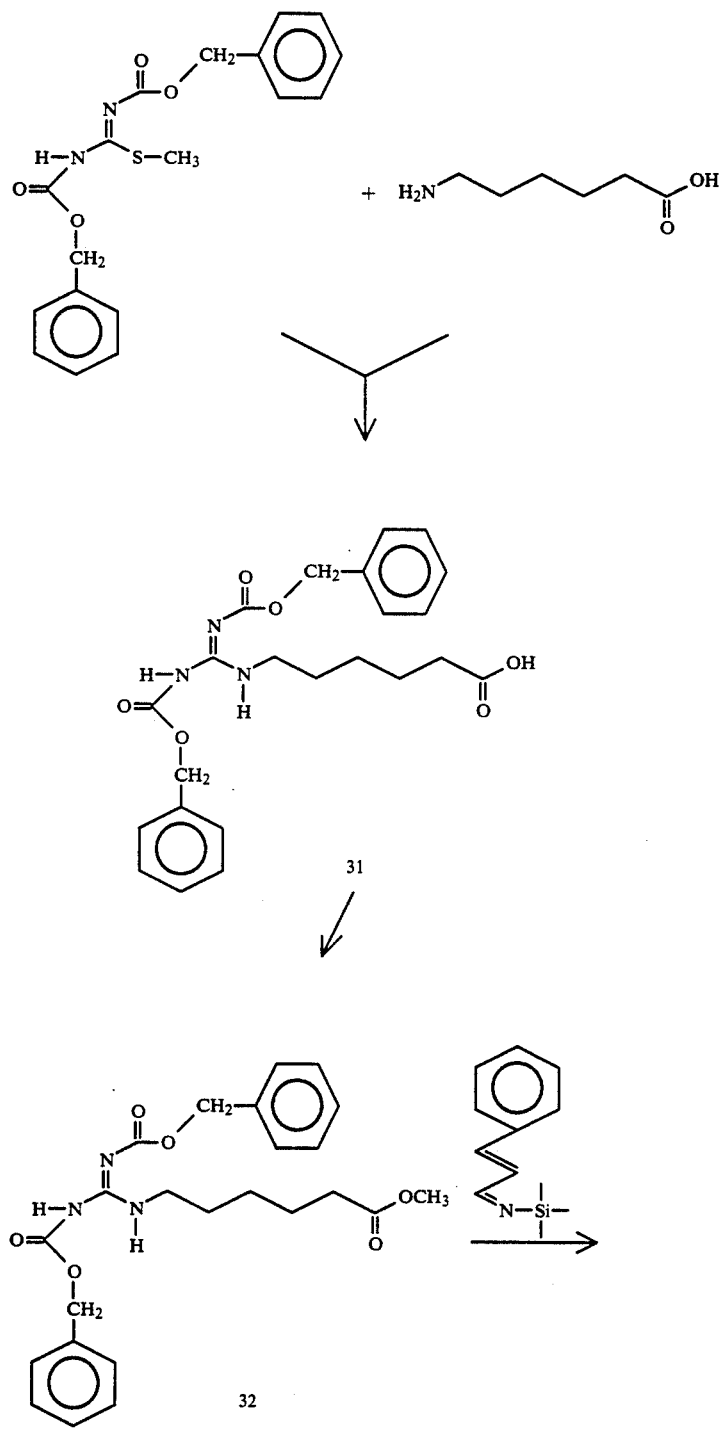

Scheme 8
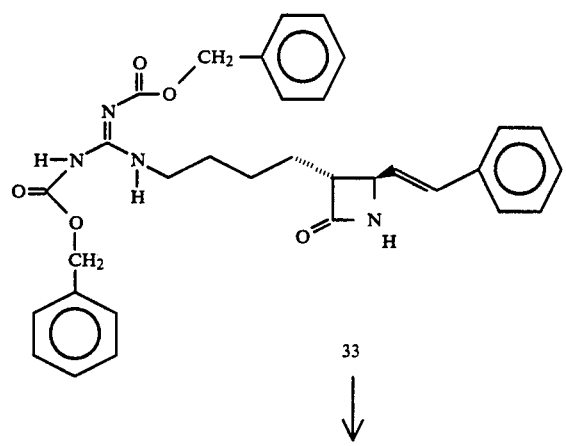
33
↓
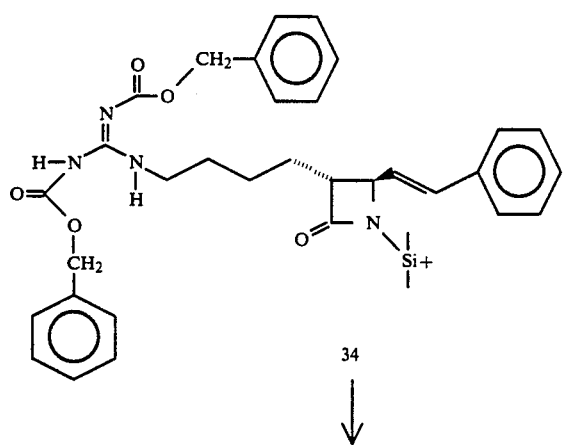
34
↓
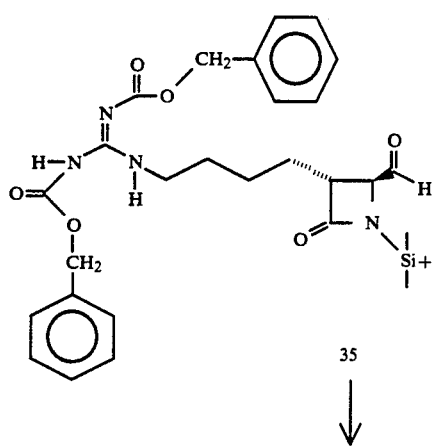
35
↓

Scheme 8
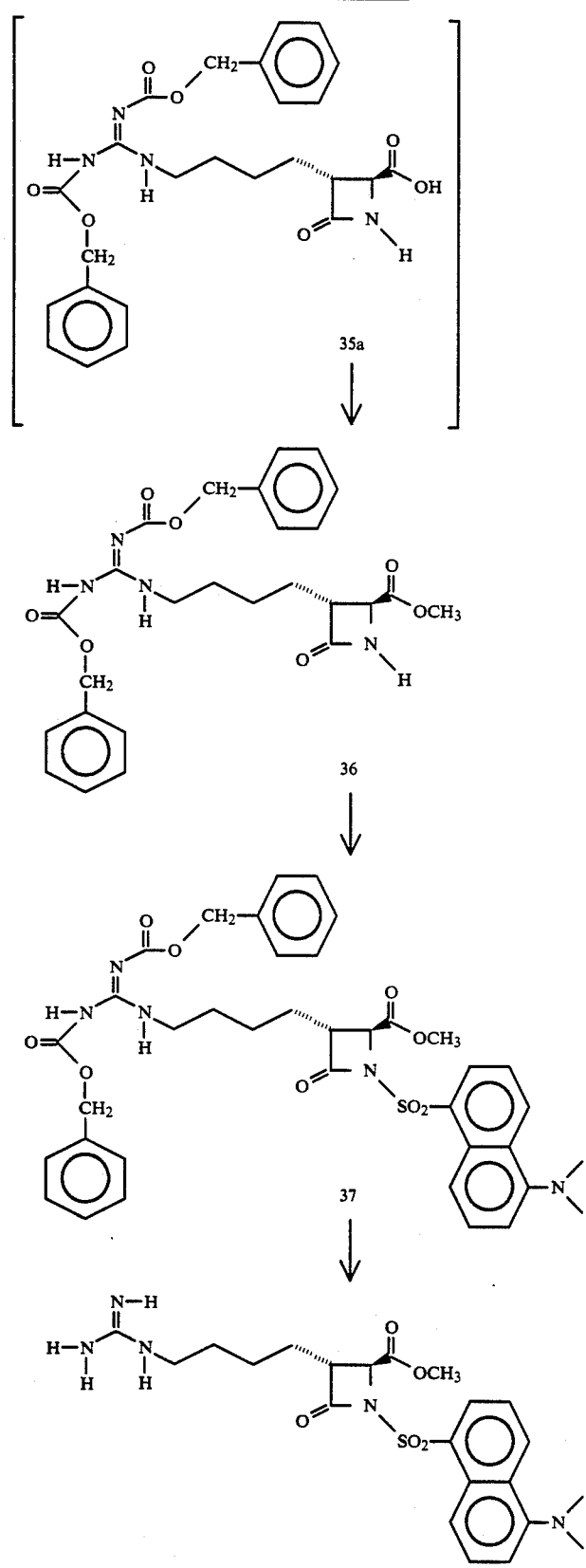
XVII

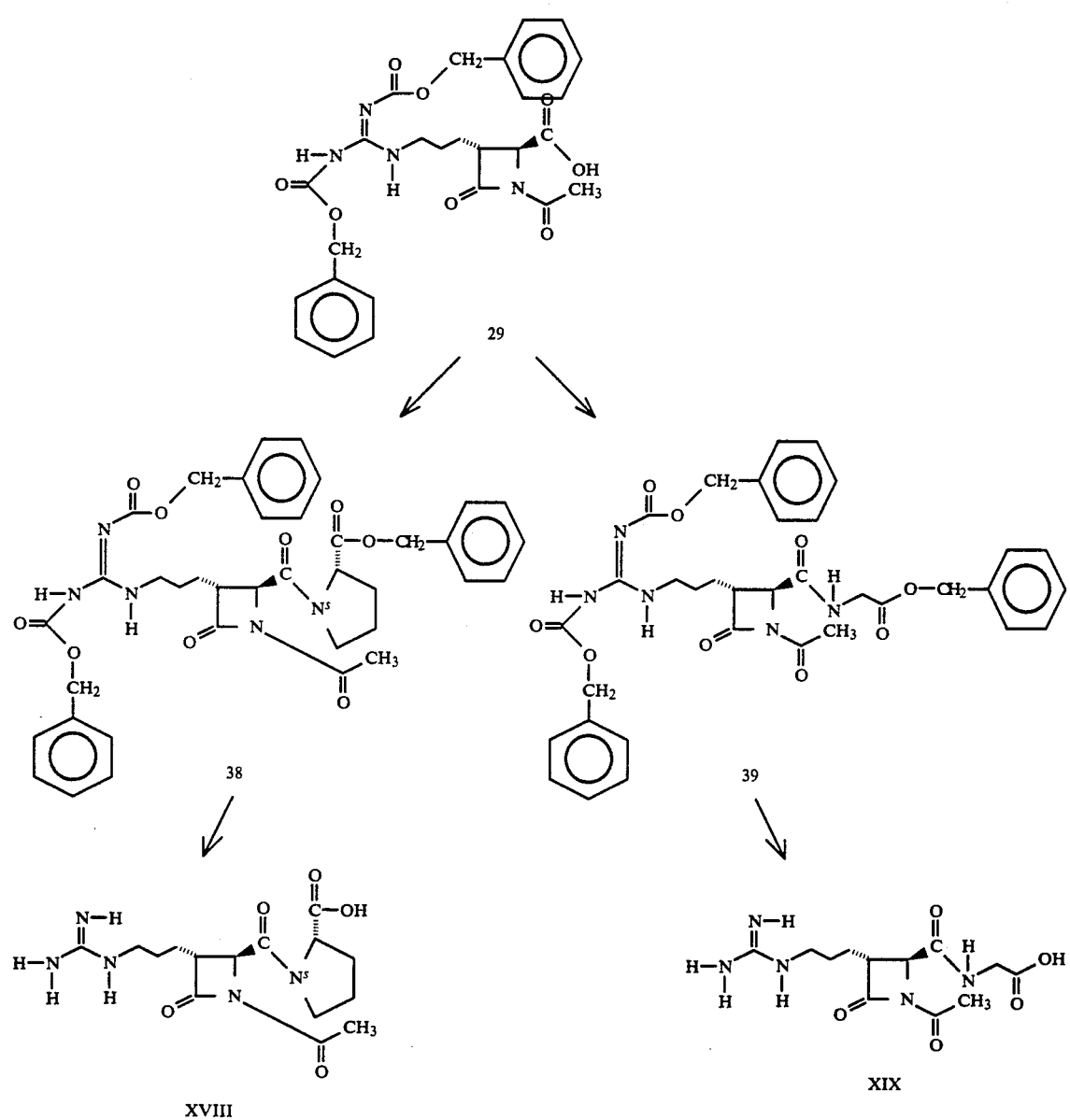
Scheme 9
Referring to Scheme 9, compound 29 is converted to compounds 38 and 39, which are catalytically hydrogenolyzed to yield compounds XVIII and XIX, respectively. In the scheme, the symbol "s" designates the configuration at the carbon atom according to the well-known Cahn-Ingold-Trelog system.

Referring to Scheme 10, compound 13 is treated with various reagents as described hereinbelow to replace the proton at the 1-position to give compounds 40, 41 and 42, each of which is then catalytically hydrogenolyzed to remove the amino protecting groups to yield compounds XX, XXI and XXII, respectively.
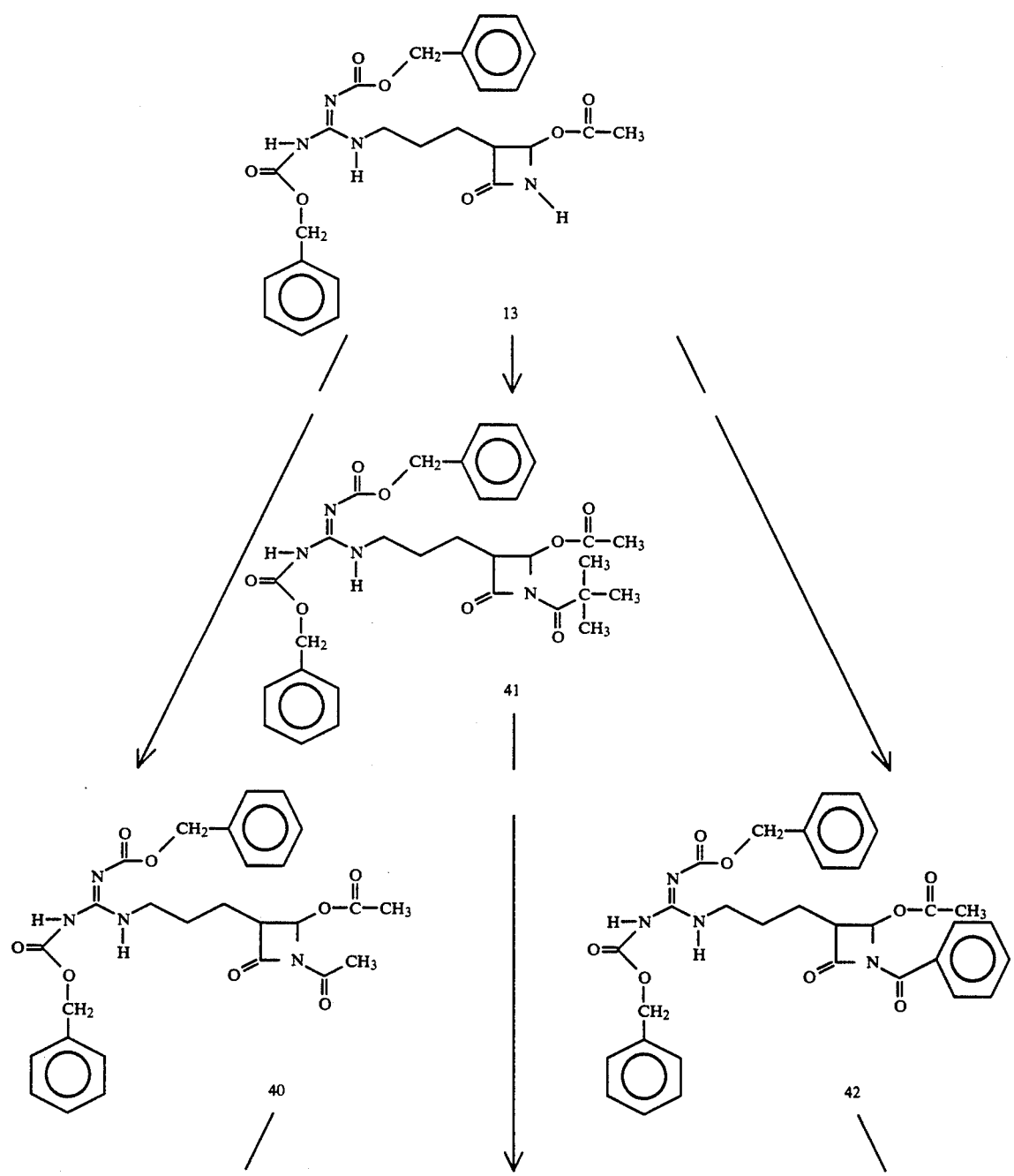
Scheme 10

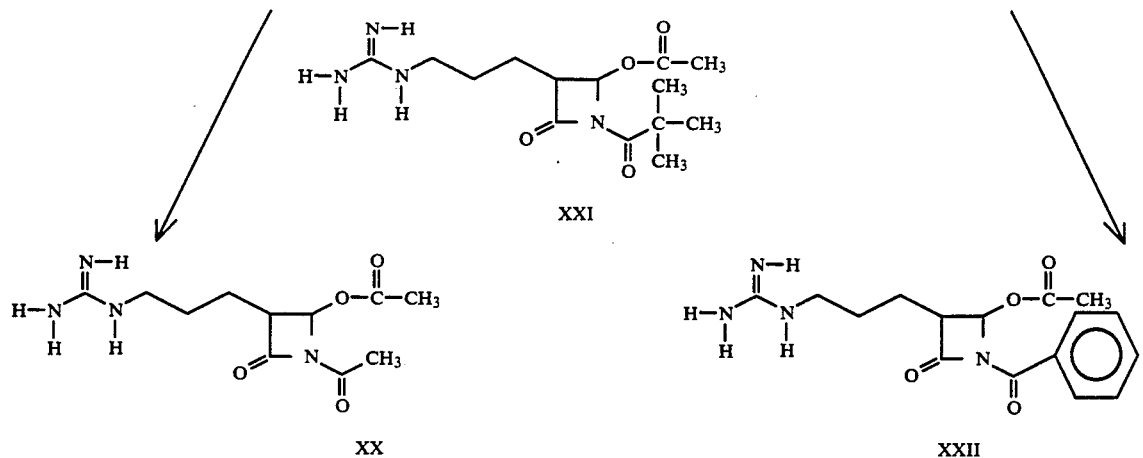
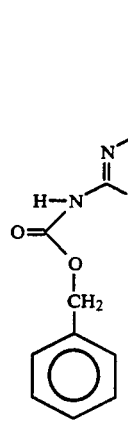
Referring to Scheme 11, compound 6b is reacted with piperidine to give compound 43 which is reacted with acetyl chloride to give compound 44. Removal of the amino protecting groups by catalytic hydrogenolysis from compound 44 yields compound XXIII.
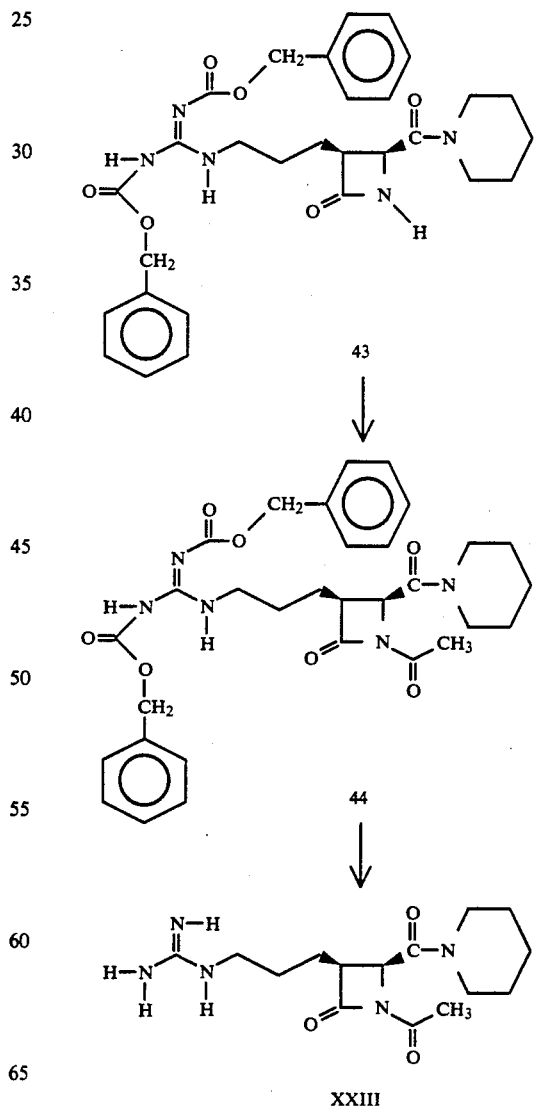

EXPERIMENTALS

In the examples which follow, melting points were recorded on a Thomas-Hoover capillary melting point apparatus and are uncorrected. All spectra were determined in CDCl$_3$, DMSO-d$_6$, CD$_3$OD, or D$_2$O unless otherwise indicated and chemical shifts are reported in ppm unit relative to the deuterated solvents used. Interproton coupling constants are reported in Hertz (Hz). Splitting patterns are designated as follows: s, singlet; d, doublet; t, triplet; q, quartet; m, multiplet; br, broad peak; dd, doublet of doublet; and dq, doublet of quartet. Infrared (IR) spectra are reported in reciprocal centimeters (cm$^{-1}$). Relative intensities are indicated as follows: s (strong), m (medium), w (weak), and br (broad).

Analytical thin-layer chromatography (TLC) was carried out on precoated silica gel plates (60F-254) and visualized using UV light, iodine vapors, and/or staining with methanolic or ethanolic phosphomolybdic acid (2% solution). Silica gel chromatography was performed in a glass column using finely divided silica gel (32–63 μm on silica gel-H) and at a pressure somewhat above atmospheric pressure with the indicated solvents. Evaporation and/or concentration of solvents were performed under a reduced pressure. EtOAC is ethyl acetate; Et$_2$O or ether is diethyl ether; AcOH is acetic acid; THF is tetrahydrofuran; DMF is dimethylformamide; MCPBA is m-chloroperbenzoic acid; U is NIH units; and Cbz is phenylmethoxylcarbonyl (or otherwise known as carbobenzyloxy) group. Celite is a registered trademark of the Johns-Manville Products Corporation for diatomaceous earth.

All hydrogenolysis was conducted under one atmospheric pressure of hydrogen unless otherwise specified.

EXAMPLE 1

5-[N′,N″-Di(Cbz)guanidino]pentanoic acid (1)

To a methanolic solution (1,000 mL) of N, N′-dicarbobenzyloxy-5-methyl-isothiourea [323 g, 0.9 mol, for the synthesis of N, N′-dicarbobezyloxy-5-methyl-isothiourea see K. Nowah et al., *Rocz. Chem.*, 43, 1953–1960 (1969)] and triethylamine (75.1 g, 0.74 mol) was added 5-aminovaleric acid (86.9 g, 0.74 mol) portionwise. The resultant suspension was refluxed for 1.5 h and concentrated. The residue was partitioned between EtOAc and saturated aqueous NaHCO$_3$ solution. The aqueous layer was acidified to pH 2.0 with hydrochloric acid and extracted with EtOAc. The organic layer was dried (MgSO$_4$) and concentrated. The residual solid was recrystallized (EtOAc/hexane) to afford 135.1 g (54% based on 5-aminovaleric acid), mp 102°–103° C.

$^1$H NMR(CDCl$_3$) δ: 8.35 (1H, br s), 7.43–7.25 (10H, m), 5.18 (2H, s), 5.13 (2H, s), 3.45 (2H, br q, J=6.5), 2.4 (2H, br t, J=4.8), 1.80 (4H, m);

IR (KBr): 1735, 1720 cm$^{-1}$;

Anal. Calcd. for C$_{22}$H$_{25}$N$_3$O$_6$: C, 61.81; H, 5.89; N, 9.83. Found: C, 61,39; H, 6.29; N, 9.92.

EXAMPLE 2

5-[N′,N″-di(Cbz)guanidino]pentanoic acid methyl ester (2)

To a 0° C. THF (700 mL) solution of compound 1 (133 g, 0.3 mol) was added carbonyldiimidazole (55.3 g, 0.34 mol). After the addition was complete, the resultant solution was allowed to warm to room temperature and stirred for 45 min. Anhydrous methanol (100 mL) was added. The solution was stirred for 16 h and concentrated. The residue was triturated with ether (400 mL). The supernatant was separated. The process was repeated with two more portions of ether (2×200 mL). The ether phases were combined, washed with H$_2$O, dried (MgSO$_4$), and concentrated. The residue was purified by silica gel chromatography (Et$_2$O:hexane/1:1) to afford 130 g (95%) of the title product, mp 36°–39° C.

$^1$H NMR (CDCl$_3$) δ: 8.36–8.28 (1H, br s), 7.46–7.21 (10H, m), 5.15 (2H, s), 5.09 (2H, s), 3.64 (3H, s), 3.42 (2H, br q, J=4.9), 2.32 (2H, br t, J=4.9), 1.24–1.50 (4H, m);

IR (KBr): 1740 cm$^{-1}$;

Anal. Calcd. for C$_{23}$H$_{27}$H$_{27}$N$_3$O$_6$: C, 62.54; H, 6.15; N, 9.51. Found: C, 62.64 H, 6.03; N, 9.37.

EXAMPLE 3 trans-4-(2-Phenylethenyl)-3-[3-[N′,N″-di(Cbz-)guanidino]propyl]-2-azetidinone (3a) and cis-4-(2-phenylethenyl)-3-[3-[N′,N″-di(Cbz)guanidino]-propyl]-2-azetidinone (3b)

To a −40° C. THF (800 mL) solution of 1,1,1,3,3,3-hexamethyldisilazane (110 g, 0.69 mol) was added 2.5M hexane solution of n-butyllithium (272 mL, 0.69 mol). The resultant solution was cooled to −78° C. followed by the addition of THF (300 mL) solution of compound 2 (106 g, 0.24 mol). After the addition was complete, the reaction mixture was allowed to warm to −30° C. and kept at this temperature for 1 h followed by cooling to −78° C. THF (100 mL) solution of N-(trimethylsilyl)-cinnamilydenimine [51.5 g, 0.25 mol, for the synthesis of N-(trimethylsilyl)cinnamilydenimine, see example 67] was added dropwise, and the resulting solution was kept at −20° C. for 16 h. (For a related addition of the β-hydroxy ester danion to cinnamilydenimine, see G. Cainelli et al., *Tetrahedron Lett.*, 26, 937 (1985)). The light green reaction mixture was concentrated to half of its original volume and diluted with ether. The solution was stirred with 5N HCl; enough acid was used to maintain the pH of the aqueous phase at 2.0. The organic phase was separated, washed with H$_2$O and brine, dried (MgSO$_4$), and concentrated- The residue was purified by silica gel chromatography to afford 50 g (38%) of the trans isomer, 5.7 g (4.4%) of the cis isomer and 26.5 g (20%) of the mixture of cis and trans isomers.

trans isomer 3a: mp 101° C.;

¹H NMR (CDCl₃) δ: 8.43 (1H, br t, J=4.0), 7.50–7.24 (15H, m), 6.66 (1H, d, J=14.5), 6.58 (1H, s), 6.27 (1H, dd, J=14.5, 8.0), 5.22 (2H, s), 5.15 (2H, s), 3.97 (1H, br d, J=8.0), 3.56–3.45 (2H, m), 3.01 (1H, m), 1.85–1.70 (4H, m);

IR (film): 1734 cm⁻¹;

Anal. Calcd. for C₃₁H₃₂N₄O₅: C, 68.86; H, 5.96; N, 10.36. Found: C, 68.91; H, 5.94; N, 10.29.

cis isomer 3b:

¹H NMR (CDCl₃) δ: 8.27 (1H, br t, J=5.6), 7.37–7.14 (15H, m), 6.12 (1H, d, J=14.5), 6.12 (1H, dd, J=14.5, 7.2), 5.95 (1H, br s), 5.07 (2H, s), 5.05 (2H, s), 4.32 (1H, br t, J=7.2), 3.48–3.25 (3H, m), 1.78–1.50 (4H, m);

IR (film): 1760, 1745 cm⁻¹;

High resolution FAB MS Calcd. for C₃₁H₃₃N₄O₅: (M+H) 541.2451. Found: 541.2441.

EXAMPLE 4 trans-4-(2-Phenylethenyl)-3-[3-[N',N''-di(Cbz-)guanidino]propyl]-1-t-butyldimethylsilyl-2-azetidinone (4a)

To a DMF (40 mL) solution of compound 3a (7.8 g, 14.4 mmol) and triethylamine (2.1 g, 21 mmol) was added t-butyldimethylsilyl chloride (3.12 g, 21 mmol). The reaction mixture was stirred at room temperature for 15 h and partitioned between Et₂O and H₂O. The organic layer was separated, washed with additional H₂O, dried (MgSO₄), and concentrated. The residue was purified by silica gel chromatography (Et₂O:hexane/1:1) to afford 8.3 g (88% of the title product.

¹H NMR (CDCl₃) δ: 8.37 (1H, t, J=4.5) 7.45–7.23 (15H, m), 6.58 (1H, d, J=16.0), 6.17 (1H, dd, J=16.0, 9.9), 5.6 (2H, s), 5.13 (2H, s), 3.86 (1H, dd, J=9.9, 1.5), 3.45–3.41 (2H, m), 3.04–2.95 (1H, m), 1.90–1.65 (4H, m), 0.88 (9H, s), 0.16 (3H, s), 0.1 (3H, s);

Anal. Calcd. for C₃₇H₄₆N₄O₅Si: C. 67.86, H, 7.08; N, 8.56. Found: C, 67.12; H, 7.06; N, 8.21;

High resolution FAB MS Calcd. for C₃₇H₄₇N₄O₅Si: (M+H) 655.3316. Found: 655.1295.

EXAMPLE 5

Step A trans-4-Formyl-3-[3-[N',N''-di(Cbz)guanidino]propyl]-1-t-butyldimethylsilyl-2-azetidinone (5a)

Ozone was passed through a −78° C. CH₂Cl₂ (650 mL) solution of compound 4a (55 g, 84 mmol) until a blue color was maintained. Excess ozone was purged with N₂. Dimethyl sulfide (60 mL) was added. The solution was allowed to warm to room temperature and to stand for 48 h. The solution was concentrated to afford the title compound which was not further purified but used directly in step B.

¹H NMR (CDCl₃) δ: 9.63 (1H, d, J=5.3), 8.40 (1H, br t, J=5.3), 7.60–7.25 (10H, m), 5.17 (2H, s), 5.13 (2H, s), 3.67 (1H, m), 3.53–3.40 (2H, m), 3.28–3.21 (1H, m), 1.93–1.65 (4H, m), 0.97 (9H, s), 0.2 (3H, s,), ) 0.13 (3H, s).

Step B trans-4-Carboxy-3-[3-[N',N''-di(Cbz)guanidino]propyl]-2-azetidinone (6a)

The aldehyde 5a prepared in Step A was dissolved in acetone (75 mL). Freshly prepared Jones reagent was added dropwise to the acetone solution, maintaining the temperature between 20°–25° C., until the TLC indicated the disappearance of the starting aldehyde. The resultant suspension was concentrated to half of its original volume and partitioned between EtOAc and H₂O. The organic phase was dried (Na₂SO₄) and concentrated. The residual solid was recrystallized from EtOAc/hexane to afford 8.8 g (54% from 4a) of the title compound as a greenish solid, mp 172°–173° C.

¹H NMR (CDCl₃) δ: 8.43(1H, br s), 8.24 (1H, s), 7.45–7.20 (10H, m), 5.17 (2H, s), 4.99 (2H, s), 3.74 (1H, d, J=1.8), 1.70–1.50 (4H, m);

High resolution FAB MS Calcd. for C₂₄H₂₇N₄O₇: (M+H) 483.1890. Found: 683.1880.

EXAMPLE 6 cis-4-(2-Phenylethenyl)-3-[3-[N',N''-di(Cbz)guanidino]propyl]-1-t-butyldimethylsilyl-2-azetidinone (4b)

To a DMF (30 mL) solution of compound 3b (5.6 g, 10.4 mmol) was added triethylamine (1.73 g 17 mmol) and t-butyldimethylsilyl chloride (1.86 g, 12 mmol). The resultant reaction mixture was stirred for 1 h followed by partitioning between Et₂O and H₂O. The organic layer was dried (MgSO₄) and concentrated. The residue was purified by silica gel chromatography (Et₂O:hexane/3:2) to afford 4.73 g (78.6%) of the title product.

¹NMR (CDCl₃) δ: 8.30 (1H, br t, J=5.4), 7.39–7.21 (15H, m), 6.57 (1H, d, J=15.2), 6.02 (1H, dd, J=15.2, 8.4), 4.11 (2H, s), 5.08 (2H, s), 4.22 (1H, dd, J=8.4, 6.09), 3.50–3.26 (3H, m), 1.84–1.51 (4H, m), 0.94 (9H, s), 0.23 (3H, s), 0.14 (3H, s);

High resolution FAB MS Calcd. for C₃₇H₄₇N₄O₅Si: (M+H) 655.3316. Found: 655.3323.

EXAMPLE 7

Step A cis-4-Formyl-3-[3-[N',N''-di(Cbz)guanidino]propyl]-1-t-butyldimethysilyl-2-azetidinone (5b)

Ozone was passed through a −78° C. methylene chloride (100 mL) solution of compound 4b (4.73 g, 7.22 mmol) until a blue color was maintained. Excess ozone was purged with nitrogen. Dimethyl sulfide (10 mL) was added. The solution was allowed to stand for 16 h and concentrated to afford the title product which was not further purified but used directly in Step B.

Step B cis4Carboxyl-3-[3-[N',N''-di(Cbz)guanidino]propyl]-2-azetidinone (6b)

Compound 5b prepared in Step A was taken up in acetone (50 mL). Jones reagent was added dropwise until the orange color persisted. The resultant reaction mixture was stirred for an additional 15 min and concentrated. The residue was partitioned between H₂O and EtOAc. The organic layer was dried (MgSO₄) and concentrated. The residue was purified by silica gel chromatography (EtOAc:Et₂O:AcOH/1:4:0.05) to afford 1.8 g (51%) of the title product.

¹H NMR (CDCl₃) δ: 8.4 (1H, br s), 7.45–7.10 (10H, m), 6.70 (1H, br s), 5.17 (2H, s), 5.07 (2H, s), 4.19 (1H, d, J=6.9), 3.50–3.10 (3H, m), 1.80–1.50 (4H, m);

High resolution FAB MS Calcd. for $C_{24}H_{27}N_4O_7$: (M+H) 483.1880. Found: 483.1878.

EXAMPLE 8 trans-4-Methoxycarbonyl-3-[3-[N',N''-di(Cbz-)guanidino]-propyl]-2-azetidinone (7)

An ether solution of diazomethane was added to a methylene chloride (50 mL) solution of compound 6a (4.69, 9.72 mmol) until the yellow color was maintained. Excess diazomethane was destroyed by letting it react with acetic acid. The solution was concentrated and the residue was purified by silica gel chromatography (EtOAc:Et$_2$O/9:1) to afford 3.41 g (71%) of the title product.

$^1$H NMR (CDCl$_3$) δ: 8.38 (1H, br t, J=5.3), 7.45–7.25 (10H, m), 6.27 (1H, br s), 5.18 (2H, s), 5.13 (2H, s), 3.88 (1H, d, J=2.4), 3.77 (3H, s), 3.54–3.42 (2H, m), 3.31–3.22 (1H, m), 1.95–1.70 (4H, m);

Anal. Calcd. for $C_{25}H_{28}N_4O_7$: C, 60.47; H, 5.68; N, 11.28. Found: C, 60.36; H, 5.76; N, 11.26.

EXAMPLE 9 trans-4-Methoxycarbonyl-3-[3-[N',N''-di(Cbz-)guanidino]-propyl]-1-p-toluenesulfonyl-2-azetidinone (8)

To a −78° C. THF (5 mL) solution of compound 7 (4.36 mg, 0.67 mmol) was added 1N THF solution of sodium bis(trimethylsilyl)amide (0.67 mL, 0.67 mmol), and the resultant solution was stirred for 15 min. p-Toluenesulfonyl chloride (134 mg, 0.70 mmol) was added, and the mixture was stirred at −78° C. for 4 h and at −20° C. for 2½ days. The reaction mixture was partitioned between EtOAc and H$_2$O. The organic layer was dried (Na$_2$SO$_4$) and concentrated. The residue was purified by silica gel chromatography (Et$_2$O:hexane/3:2) to afford 210 mg (48%) of the title product.

$^1$H NMR (CDCl$_3$) δ: 8.32 (1H, br t, J=6.1 ), 7.88 ( 1H, d, J=8.4), 7.40–7.20 (14H, m), 5.10 (2H, s), 5.06 (2H, s), 4.98 (1H, br s), 4.28 (1H, d, J=1.5), 3.72 (3H, s), 3.45–3.33 (2H, m), 3.23–3.13 (1H, m), 2.42 (3H, s), 1.85–1.55 (4H, m);

IR (film): 1805, 1735 cm$^{-1}$;

Anal. Calcd. for $C_{32}H_{34}N_4O_9S$: C, 58.77; H, 5.14; N, 8.14 Found: C, 59.06; H, 5.26; N, 8.61.

EXAMPLE 10 trans-4-Methoxycarbonyl-3-(3-guanidinopropyl)-1-p-toluenesulfonyl-2-azetidinone hydrochloride salt (I)

An ethyl acetate/methanol (2.5 mL/2.5 mL) solution of compound 8 (197 mg, 0.3 mmol) and 1N HCl (0.6 mL), containing palladium on carbon catalyst, was stirred under one atmosphere of hydrogen until TLC indicated the disappearance of the starting 8. The suspension was filtered through a pad of Celite, and the filtrate was concentrated to afford 30 mg (24%) of the title product as a foam.

$^1$H NMR (CD$_3$OD) δ: 7.88 (2H, d, J=8.5 ), 7.44 (2H, d, J=8.5), 4.47 (1H, d, J=3.6), 3.74 (3H, s), 3.42 (1H, dt, J=7.2, 3,6), 3.16 (2H, t, J=6.6), 2.46 (3H, s), 1.86–1.56 (4H, m);

IR (film): 1800, 1755 cm$^{-1}$;

Anal. Calcd. for $C_{16}H_{24}N_4O_5Cl$: C, 44.18; H, 5.33; N, 12.88; Cl, 8.15; Found: C, 43.79; H, 5.62; N, 12.52; Cl, 8.01;

High resolution FAB MS Calcd. for $C_{16}H_{24}N_4O_5$: (M+H) 383.1389. Found: 383.1376.

EXAMPLE 11 trans-4-Methoxycarbonyl-3-[3-[N',N''-di(Cbz-)guanidino]propyl]-1-acetyl-2-azetidinone (9)

Acetyl chloride (9.5 g, 0.12 mol) was added to a −10° C. methylene chloride (50 mL) solution of compound 7 (2.0 g, 4.0 mmol). Triethylamine (12.3 g, 0.12 mol) was added dropwise with vigorous stirring of the reaction mixture. After the addition was complete, the resultant suspension was stirred for an additional 2 h at room temperature and then washed with H$_2$O. The organic phase was separated, washed with saturated aqueous NaHCO$_3$ solution, dried (Na$_2$SO$_4$), and concentrated. The residue was purified by silica gel chromatography (CH$_2$Cl$_2$:MeOH/99.5:0.5) to afford 700 mg (36%) of the title product.

$^1$H NMR δ: 8.32 (1H, br t, J=5.0), 7.37–7.20 (10H, m), 5.16 (2H, s), 5.07 (2H, s), 4.08 (1H, d, J=2.3), 3.37 (3H, s), 3.47–3.38 (2H, m), 3.26–3.15 (1H, m), 2.34 (3H, s), 1.93–1.60 (4H, m);

IR (film): 1800, 1740, 1720 cm$^{-1}$;

High resolution FAB MS Calcd. for $C_{27}H_{31}N_4O_8$: (M+H) 539.2125. Found: 539.2162.

EXAMPLE 12 trans-4-Methoxycarbonyl-3-(3-guanidinopropyl)-1-acetyl-2-azetidinone hydrochloride salt (II)

A methanol/ethyl acetate (2.5 mL/2.5mL) solution of compound 9 (313 mg, 0.58 mmol) and 1N HCl (0.58 mL) was stirred under a hydrogen atmosphere with 10% palladium on carbon catalyst. When the starting material had disappeared as determined by TLC, the reaction mixture was passed through a pad of Celite and the filtrate was concentrated to afford 150 mg (84%) of the title product as a yellow foam.

$^1$H NMR (CD$_3$OD) δ: 4.27 (1H, d, J=3.1) 3.78 (3H, s), 3.50–3.10 (3H, m), 2.35 (3H, s), 1.90–1.60 (4H, m);

IR (film): 1800 cm$^{-1}$;

High resolution FAB MS Calcd. for $C_{11}H_{18}O_4$: (M+H) 271.1406. Found: 271.1414.

EXAMPLE 13 trans-4-Methoxycarbonyl-3-[3-[N',N''-di(Cbz-)guanidino]propyl]-1-[(5-dimethylamino)-1-naphthalenesulfonyl]-2-azetidinone (10)

To a −78° C. THF (5 mL) solution of compound 7 (1.03 g, 2.08 mmol) was added 1N THF solution of sodium bis(trimethylsilyl)amide (2.08 mL, 2.08 mmol), and the resultant solution was stirred for 20 min. Dansyl chloride (0.5 g, 2.08 mmol) was added. The mixture was allowed to warm to room temperature, stirred for 1 h, and partitioned between EtOAc and pH 7.0 aqueous buffer. The organic layer was dried (Na$_2$SO$_4$) and concentrated. The residue was purified by silica gel chromatography (Et$_2$O) to afford 0.45 g (30%) of the title product.

$^1$H NMR (CDCl$_3$) δ: 8.61 (1H, d, J=8.4), 8.47 (1H, d, J=9.2), 8.28 (1H, d, J=6.9), 7.63–7.49 (2H, m), 7.45–7.15 (11H, m), 5.16 (2H, s), 5.08 (2H, s), 4.22 (1H, d, J=2.3), 3.46 (3H, s), 3.42–3.33 (2H, m), 3.31–3.24 (1H, m), 2.84 (6H, s), 1.86–1.53 (4H, m);

IR (KBr): 1810, 1755 cm$^{-1}$;

FAB MS: 730 (M+H, base).

EXAMPLE 14 trans-4-Methoxycarbonyl-3-(3-guanidinopropyl)-1-[(5-dimethylamino)-1-naphthalenesulfonyl]-2-azetidinone hydrochloride salt (III)

A methanol/ethyl acetate (5 mL/2 mL) solution of compound 10 (0.45 g, 0.62 mmol) and 1N HCl (0.7 mL), containing 10% palladium on carbon catalyst, was stirred under hydrogen. When the starting material had disappeared as determined by TLC (25 min), the reaction mixture was passed through a pad of Celite and the filtrate was concentrated to afford 276 mg (89%) of the title product.

$^1$H NMR (CD$_3$OD) δ: 8.46 (1H, d, J=8.4), 8.38 (1H, d, J=9.2), 8.08 (1H, d, J=7.7), 7.53–7.40 (2H, m), 7.28 (1H, br d, J=6.9), 4.20 (1H, d, J=2.3), 3.19 (3H, s), 3.09–1.84 (3H, m), 2.77 (6H, s), 1.60–1.30 (4H, m);

IR (KBr): 1805, 1755 cm$^{-1}$;

High resolution FAB MS Calcd. for C$_{21}$H$_{28}$N$_5$O$_5$S: (M+H) 462.1811. Found: 462.1801.

EXAMPLE 15 trans-4-Methoxycarbonyl-3-[3-[N',N''-di(Cbz)guanidino]propyl]-1-methylsulfonyl-2-azetidinone (11)

To a vigorously stirred methylene chloride (10 mL) solution of compound 7 (0.8 g, 1.6 mmol) and triethylamine (4.86 g, 48 mmol) was added methanesulfonyl chloride (5.52 g, 48 mmol) dropwise. The reaction mixture was diluted with additional CH$_2$Cl$_2$ and washed with pH 7.0 aqueous buffer. The organic phase was dried (Na$_2$SO$_4$) and concentrated. The residue was purified by silica gel chromatography (CH$_2$Cl$_2$: MeOH/99:1) to afford 340 mg (37%) of the title compound.

$^1$H NMR (CDCl$_3$) δ: 7.40–7.13 (10H, m), 5.16 (2H, s), 5.10 (2H, s), 4.35 (1H, d, J=3.18), 3.80 (3H, s), 3.46 (2H, d, J=6.6), 3.3 (3H, s), 3.28–3.25 (1H, m), 1.95–1.73 (4H, m);

IR (film): 1808, 1745 cm$^{-1}$;

High resolution FAB MS Calcd. for C$_{26}$H$_{31}$N$_4$O$_9$S: (M+H) 575.1812. Found: 575.1801.

EXAMPLE 16 trans-4-Methoxycarbonyl-3-(guanidinopropyl)-1-methylsulfonyl-2-azetidinone hydrochloride salt (IV)

A methanol solution of compound 11 (0.29 g, 0.5 mmol) and 1N HCl (0.5 mL), containing 10% palladium on carbon, was stirred under 35 psi of hydrogen atmosphere for 2 h. The suspension was filtered through a pad of Celite and the filtrate was concentrated to afford 52 mg (30%) of the title product.

$^1$H NMR (CD$_3$OD) δ: 4.56 (1H, s), 3.83 (3H, s), 3.54–3.18 (3H, m), 3.30 (3H, s), 1.96–1.63 (4H, m);

IR (film): 1810, 1755 cm$^{-1}$;

High resolution FAB MS Calcd. for C$_{10}$H$_{19}$O$_5$N$_4$S: (M+H) 307.1076. Found: 307.1066.

EXAMPLE 17 trans-4-Methoxycarbonyl-3-[3-[N',N''-di(Cbz)guanidino]propyl]-1-phenylaminocarbonyl-2-azetidinone (12)

To a THF (10 mL) solution of compound 7 (690 mg, 1.38 mmol) at −78° C. was added 1N THF solution of sodium bis(trimethylsilyl) amide (0.149 mL, 0.149 mmol), and the resultant mixture was stirred for 10 min. Phenylisocyanate (0.149 mL, 1.38 mmol) was added, followed by warming the solution to room temperature and stirring for 1 h. The solution was concentrated, and the residue was partitioned between pH 4.0 aqueous buffer and ethyl acetate. The organic phase was dried (MgSO$_4$) and concentrated. The residue was purified by silica gel chromatography (Et$_2$O:hexane/3:1) to afford 450 mg (53%) of the title product as a white foam.

$^1$H NMR (CDCl$_3$) δ: 7.53–7.03 (15H, m), 5.17 (2H, s), 5.05 (2H, s), 4.23 (1H, d, J=2.3), 3.78 (3H, s), 3.53–3.40 (2H, m), 3.36–3.26 (1H, m), 2.0–1.68 (4H, m);

IR (KBr): 1780, 1732 cm$^{-1}$;

High resolution FAB MS Calcd. for C$_{32}$H$_{34}$H$_5$O$_8$: (M+H) 616.2407. Found: 616.2413.

EXAMPLE 18 trans-4-Methoxycarbonyl-3-(3-guanidinopropyl)-1-phenylaminocarbonyl-2-azetidinone hydrochloride salt (V)

A methanol/ethyl acetate (2.5 mL/2.5 mL) solution of compound 12 (421 mg, 0.68 mmol) and 1N HCl (0.68 mL), containing 10% palladium on carbon, was stirred under a hydrogen atmosphere for 1 h. The reaction mixture was filtered through a pad of Celite, and the filtrate was concentrated to afford 270 mg (quantitative) of the title product as a yellow foam.

$^1$H NMR (CD$_3$OD) δ: 7.49–7.09 (5H, m), 4.38 (1H, d, J=2.8), 3.82 (3H, s), 3.51–3.21 (3H, m), 1.98–1.73 (4H, m);

IR (KBr): 1780, 1740 cm$^{-1}$;

High resolution FAB MS Calcd. for C$_{16}$H$_{22}$O$_4$N$_5$: (M+H) 348.1672. Found: 348.1679.

EXAMPLE 19

4-Acetyloxy-3-[3-[N',N''-di(Cbz)guanidino]propyl]-2-azetidinone (13)

Compound 6a (26.1 g, 54 mmol) was dissolved in a solution of acetic acid (105 mL) and DMF (15 mL) with warming. The resultant greenish solution was cooled to room temperature, followed by addition of lead tetraacetate (71.5 g, 160 mmol) in small portions. The suspension was stirred for 5 h at 60° C. and concentrated. The residue was resuspended in methylene chloride and filtered through a pad of Celite. The filtrate was concentrated, and the residue was purified by silica gel chromatography (Et$_2$O:hexane/3:2) to afford 15.5 g (57%) of the title product as a mixture of trans and cis (2:1) isomers.

$^1$H NMR (CDCl$_3$) δ: 7.37–7.18 (10H, m), 5.78($\frac{1}{3}$H, d, J=3.0), 5.46 ($\frac{2}{3}$ H, br s), 5.13 (2H, s), 5.07 (2H, s), 3.45-3.36 (2H, m), 3.15-3.08 (1H, m), 2.07 (1H, s), 2.05 (2H, s);

High resolution FAB MS Calcd. for $C_{25}H_{29}N_4O_7$: 497.2036. Found: 497.2031.

EXAMPLE 20 trans-4-Phenylthio-3-[3-[N',N''-di(Cbz)guanidino]-propyl]-2-azetidinone (14)

To a THF (20 mL) suspension of sodium thiophenoxide formed from NaH (190 mg, 4.90 mmol, 60% oil dispersion) and thiophenol (0.54 g, 4.9 mmol) was added compound 13 (1.22 g, 2.45 mmol). The resultant solution was stirred for 30 min and concentrated under vacuo. The residue was partitioned between ethyl acetate and water. The organic layer was dried (MgSO$_4$) and concentrated. The residue was purified by silica gel chromatography (Et$_2$O:hexane/3:1) to afford 450 mg (34%) of the title product.

$^1$H NMR (CDCl$_3$) δ: 8.37-8.26 (1H, br s), 7.48-7.20 (15H, m), 6.47 (1H, br s), 5.17 (2H, s), 5.10 (2H, s), 4.64 (1H, br s), 3.52-3.36 (2H, m), 3.07-2.96 (1H, m), 3.07-2.96 (1H, m), 1.85-1.55 (4H, m);

IR (film): 1770, 1740 cm$^{-1}$.

EXAMPLE 21

Step A tans-4-Phenylthio-3-[3-[N',N''-di(Cbz)guanidino]-propyl]-1-acetyl-2-azetidinone (15)

To a −78° C. THF (7 mL) solution of compound 14 (450 mg, 0.82 mmol) was added 1N THF solution of sodium bis(trimethylsilyl)amide (0.8 mL) dropwise. The resultant solution was stirred for 10 min, followed by the addition of acetyl chloride (0.054 mL, 0.76 mmol). The resultant solution was warmed to room temperature and stirred for an additional 30 min and concentrated- The residue was partitioned between ethyl acetate and H$_2$O. The organic phase was dried (MgSO$_4$) and concentrated to afford 450 mg (93%, crude yield) of the title compound which was directly used in Step B.

$^1$H NMR (CDCl$_3$) δ: 8.27 (1H, br t, J=5.3), 7.53-7.20 (15H, m), 5.12(2H, s), 5.08 (2H, s), 4.82 (1H, d, J=2.3), 3.38 (2H, q, J=6.9), 3.03 (1H, dt, J=8.4, 2.3), 2.32 (3H, s), 1.80-1.52 (4H, m);

IR (film): 1800, 1730 (br) cm$^{-1}$;

High resolution FAB MS Calcd. for $C_{31}H_{33}N_4O_6S$: 589.2121. Found: 589.2111.

Step B trans-4-Phenylsulfonyl-3-[3-[N',N''-di(Cbz)guanidino]-propyl]-1-acetyl-2-azetidinone (16)

To a methylene chloride (10 mL) solution of compound 15 (450 mg, 0.76 mmol) was added MCPBA (323 mg, 1.52 mmol, 80% purity), and the resultant solution was stirred for 20 min. The solution was concentrated, and the residue was partitioned between saturated aqueous NaHCO$_3$ solution and ethyl acetate. The organic layer was dried (MgSO$_4$) and concentrated. The residue was chromatographed by silica gel chromatography (Et$_2$O:hexane/3:1) to afford 210 mg (44%) of the title compound.

$^1$H NMR (CDCl$_3$) δ: 8.40-8.30 (1H, br t), 7.92-7.20 (15H, m), 5.15 (2H, s), 5.08 (2H, s), 4.90 (1H, d, J=2.3), 3.89-3.80 (1H, m), 3.55-3.40 (2H, m), 2.28 (3H, s), 1.95-1.65 (4H, m);

IR (KBr): 1815, 1715 cm$^{-1}$;

High resolution FAB MS Calcd. for $C_{15}H_{21}N_4O_4S$: 353.128. Found: 353.1281

EXAMPLE 22 trans-4-Phenylsulfonyl-3-guanidinopropyl-1-acetyl-2-azetidine hydrochloride salt (VI)

A methanol/ethyl acetate (12.5 mL/12.5 mL) solution of compound 16 (210 mg, 0.34 mmol) and 1N HCl (0.34 mL), containing 10% palladium on carbon, was stirred under a hydrogen atmosphere. After the disappearance of the starting material as determined by TLC, the reaction mixture was filtered through a pad of Celite and the filtrate was concentrated to afford 100 mg (76%) of the title product as colorless foam.

$^1$H NMR (CD$_3$OD) δ: 8.03-7.60 (5H, m), 5.29 (1H, d, J=2.9), 3.83-3.76 (1H, m), 3.22 (2H, t, J=6.9), 2.26 (3H, s), 2.01-1.70 (4H, m);

IR (KBr): 1815, 1730 cm$^{-1}$;

High resolution FAB MS Calcd. for $C_{15}H_{21}N_4O_4S$: (M+H) 353.1284. Found: 353.1281.

EXAMPLE 23 trans-4-Ethylthio-3-[3-[N',N''-di(Cbz)guanidino]-propyl]-2-azetidinone (17)

To a 0° C. suspension of NaH (60% oil dispersion, 200 mg, 498 mmol) in THF (20 ml) was added ethanethiol (0.37 mL, 4.98 mmol). The resultant mixture was stirred for 10 min, cooled to −20° C., and compound 13 (1.9 g, 3.83 mmol) was added. The solution was stirred further for 30 min at room temperature and concentrated. The residue was partitioned between ethyl acetate and pH 7.0 aqueous buffer. The organic phase was washed with brine, dried (Na$_2$SO$_4$), and concentrated. The residue was purified by silica gel chromatography (Et$_2$O) to afford 718 mg (36%) of the title product.

$^1$H NMR (CDCl$_3$) δ: 7.40-7.20 (10H, m), 5.14 (2H, s), 5.07 (2H, s), 4.43 (1H, d, J=1.5), 3.50-3.40 (2H, m), 3.13-3.05 (1H, m), 2.57 (2H, q, J=7.7), 1.85-1.60 (4H, m), 1.23 (3H, t, J=7.7);

IR (film): 1764, 1738 cm$^{-1}$;

High resolution FAB MS Calcd. for $C_{25}H_{31}N_4O_5S$: 499.2015. Found: 499.2010.

EXAMPLE 24 trans-4-Ethylthio-3-[3-[N',N''-di(Cbz)guanidino]-propyl]-1-acetyl-2-azetidinone (18)

To a −78° C. THF (10 mL) solution of compound 17 (718 mg, 1.26 mmol) was added 1N THF solution (1.5 mL) of lithium bis(trimethylsilyl)amide (1.5 mmol), followed by stirring the solution for 10 min. Acetyl chloride (0.1 mL, 1.5 mmol) was added, and the resultant solution was warmed to room temperature, followed by an additional hour of stirring. The reaction mixture was concentrated, and the residue was partitioned between pH 7.0 aqueous buffer and ethyl acetate. The organic phase was washed with brine, dried (Na$_2$SO$_4$), and concentrated. The residue was purified by silica gel chromatography (1:1/Et$_2$O:hexane) to afford 615 mg (90%) of the title product.

$^1$H NMR (CDCl$_3$) δ: 7.42–7.22 (10H, m), 5.16 (2H, s), 5.08 (2H, s), 4.75 (1H, d, J=2.3), 3.52–3.40 (2H, m), 3.07–2.84 (3H, m), 2.33 (3H, s), 1.90–1.65 (4H, m);

High resolution FAB MS Calcd. for C$_{27}$H$_{33}$N$_4$O$_6$S: (M+H) 541.2121. Found: 541.2114.

EXAMPLE 25 trans-4-Ethylthio-3-guanidinopropyl-1-acetyl-2-azetidinone hydrochloride salt (VII)

A methanol/ethyl acetate (1.5 mL/1.5 mL) solution of compound 18 (117 mg, 0.19 mmol) and 1N HCl (0.19 mL), containing 10% palladium on carbon, was stirred under a hydrogen atmosphere until TLC indicated the disappearance of the starting material (about 1 h). The suspension was filtered through a pad of Celite, and the filtrate was concentrated to afford 40 mg (68%) of the title product as a foam.

$^1$H NMR (CD$_3$OD) δ: 4.93 (1H, d, J=3.6), 3.40–2.82 (5H, m), 2.32 (3H, s), 1.95–1.63 (4H, m), 1.27 (3H, t, J=7.4);

IR (film): 1795, 1735, 1713 cm$^{-1}$;

High resolution FAB MS Calcd. for C$_{11}$H$_{21}$N$_4$O$_2$S: (M+H) 273.1385. Found: 273.1391.

EXAMPLE 26

3-[N',N''-di(Cbz)guanidino]propyl-2-azetidinone (19)

A dioxane (100 mL) solution of compound 17 (1.8 g, 3.5 mmol) containing Raney-Nickel (Aldrich) was stirred and heated for 30 min at 60° C. The Raney-Nickel was filtered, and the filtrate was concentrated. The residue was purified by silica gel chromatography to afford 830 mg (45%) of the title product.

$^1$H NMR (CDCl$_3$) δ: 7.38–7.17 (10H, m), 5.13 (2H, s), 5.05 (2H, s), 3.47–3.35 (2H, m), 3.33 (1H, t, J=5.4), 3.23–3.14 (1H, m), 3.94–3.88 (1H, m), 1.80–1.57 (4H, m);

IR (film): 1755 (shoulder), 1740 cm$^{-1}$;

High resolution FAB MS Calcd. for C$_{23}$H$_{27}$N$_4$O$_5$: (M+H) 439.1981. Found: 439.1976.

EXAMPLE 27

3-[N',N''-di(Cbz)guanidino]propyl-1-acetyl-2-azetidinone (20)

To a −78° C. THF (6 mL) solution of compound 19 (366 mg, 0.84 mmol) was added 1N THF solution of lithium bis(trimethylsilyl)amide (1 mL, 1 mmol), followed by 10 min of stirring. Acetyl chloride (0.071 mL, 1 mmol) was added, and the solution was warmed to room temperature, followed by 1 h of stirring. The solution was partitioned between ether and pH 7.0 aqueous buffer. The organic phase was dried (Na$_2$SO$_4$) and concentrated. The residue was purified by silica gel chromatography (9:1/EtO$_2$:hexane) to afford 255 mg (63%) of the title product.

$^1$H NMR (CDCl$_3$) δ: 7.40–7.18 (10H, m), 5.14 (3/2H, s), 5.12 (½H, s), 5.07 (3/2H, s), 5.05 (½H, s), 3.70–3.60 (1H, m), 3.48–3.35 (2H, m), 3.30–3.15 (2H, m), 2.33 (9/4H, s), 2.32 (¾H, s), 1.96–1.63 (4H, m);

IR (film): 1792, 1740, 1710 cm$^{-1}$;

High res. FAB MS Calcd. for C$_{25}$H$_{29}$N$_4$O$_6$: (M+H) 481.2087. Found: 481.2076.

EXAMPLE 28

3-Guanidinopropyl-1-acetyl-2-azetidinone hydrochloride salt (VIII)

A methanol/ethyl acetate (2.5 mL/2.5 mL) solution of compound 20 (255 mg, 0.58 mmol) and 1N HCl (0.58 mL), containing 10% palladium on carbon, was stirred under a hydrogen atmosphere until TLC indicated the disappearance of the starting material (about 10 min). The suspension was filtered through a pad of Celite, and the filtrate was concentrated to afford 99 mg (69%) of the title compound as a yellow foam.

$^1$H NMR (CD$_3$OD) δ: 3.70 (1H, t, J=6.7), 3.40–3.16 (4H, m), 2.31 (3H, s), 1.87–1.65 (4H, m);

IR (film): 1790, 1700 (shoulder), 1670 cm$^{-1}$;

High resolution FAB MS Calcd. for C$_8$H$_{17}$N$_4$O$_2$: (M+H) 213.1352. Found: 213.1349.

EXAMPLE 29

3-[3-[N',N''-di(Cbz)guanidino]propyl]-1-[(5-dimethylamino)-1-naphthalenesulfonyl]-2-azetidinone (21)

To a −78° C. THF (5 mL) solution of compound 19 (650 mg, 1.48 mmol) was added 1N THF solution of lithium bis(trimethylsilyl)amide (1 mL, 1 mmol), followed by 10 min of stirring. Dansyl chloride (399 mg, 1.48 mmol) was added. The resultant solution was warmed to room temperature, stirred for 1 h, and concentrated. The residue was partitioned between ethyl acetate and pH 7.0 aqueous buffer. The organic phase was washed with brine, dried (Na$_2$SO$_4$), and concentrated. The residue was purified by silica gel chromatography (4:1/Et$_2$O:hexane) to afford 186 mg (19%) of the title compound.

$^1$H NMR (CDCl$_3$) δ: 8.56 (1H, d, J=9.2), 8.33 (1H, d, J=9.2), 8.28 (1H, d, J=6.9), 7.57–7.47 (2H, m), 7.35–7.20 (10H, m), 5.13 (2H, s), 5.05 (2H, s), 3.67–3.59 (1H, m), 3.34–3.16 (3H, m), 2.80 (6H, s), 1.70–1.47 (4H, m);

IR (KBr): 1798, 1738 cm$^{-1}$;

High resolution FAB MS Calcd. for C$_{37}$H$_{38}$N$_5$O$_7$S: (M+H) 672.2492. Found: 672.2479.

EXAMPLE 30

3-Guanidinopropyl-1-[(5-dimethylamino)-1-naphthanesulfonyl)]-2-azetidinone hydrochloride salt (IX)

A methanol/ethyl acetate (2.5 mL/2.5 mL) solution of compound 21 (186 mg, 0.28 mmol) and 1N HCl (0.28 mL), containing 10% palladium on carbon, was stirred under a hydrogen atmosphere until TLC indicated the disappearance of the starting material. The suspension was filtered through a pad of Celite, and the filtrate was concentrated to afford 90 mg (73%) of the title product.

$^1$H NMR (CD$_3$OD) δ: 8.59 (1H, d, J=7.7), 8.45 (1H, d, J=7.6) 8.27 (1H d, J=7.4) 7.68–7.57 (2H m), 7.41 (1H, d, J=7.5), 3.64 (1H, t, J=5.9), 3.31–2.99 (3H, m), 2.93 (6H s) 1.61–1.43 (4H, m);

IR (film): 1795 cm$^{-1}$;

High resolution FAB MS Calcd. for C$_{19}$H$_{26}$N$_5$O$_5$S: (M+H): 404.1756. Found: 404.1752.

EXAMPLE 31 trans-4-Ethylsulfonyl-3-[3-[N,N''-di(Cbz)guanidino]-propyl]-1-acetyl-2-azetidinone (22)

To a methylene chloride (5 mL) solution of compound 18 (469 mg, 0.77 mmol) was added MCPBA (85% pure, 500 mg, 1.93 mmol) in one portion (exothermic). The resultant suspension was stirred for 30 min and partitioned between more methylene chloride and aqueous saturated sodium bicarbonate solution. The organic layer was dried ($Na_2SO_4$) and concentrated. The residue was purified by silica gel chromatography to afford 386 mg (88%) of the title product.

$^1$H NMR (CDCl$_3$) δ: 7.42–7.30 (10H, m), 5.16 (2H, s), 5.10 (2H, AB quartet), 4.93 (1H, d J=2.3) 3.80–3.70 (1H, m), 3.62–3.18 (4H, m), 2.40 (3H, s), 1.98–1.67 (4H, m), 1.38 (3H, t, J=8.4);

IR (KBr): 1780, 1700 cm$^{-1}$;

High resolution FAB MS Calcd. for $C_{11}H_{21}N_4O_4S$: (M+H) 305.1284. Found: 305.1276.

EXAMPLE 32 trans-4-Ethylsulfonyl-3-guanidinopropyl-1-acetyl-2-azetidinone hydrochloride salt (X)

A methanol/ethyl acetate (2.5 mL/2.5 mL) solution of compound 22 (380 mg, 0.66 mmol) and 1N HCl (0.66 mL), containing 10% palladium on carbon, was stirred under a hydrogen atmosphere until TLC indicated the disappearance of the starting material. The suspension was filtered through a pad of Celite, and the solution was concentrated to afford 140 mg (62%) of the product as a yellow foam.

$^1$H NMR (CD$_3$OD) δ: 5.27 (1H, d, J=3.1), 3.76–3.70 (1H, m), 3.49–3.19 (4H, m), 2.39 (3H, s), 2.02–1.73 (1H, m), 1.42 (3H, t, J=7.4);

IR (film): 1810, 1720 cm$^{-1}$;

High resolution FAB MS Calcd. for $C_{11}H_{21}N_4O_4S$: (M+H) 305.1284. Found: 305.1276.

EXAMPLE 33 trans-4-(1-Piperidinocarbonyl)-3-[3-[N',N''-di(Cbz)-guanidino]-propyl]-2-azetidinone (23)

To a THF (20 mL) solution of compound 6a (1.0 g, 2.1 mmol) was added carbonyldiimidazole (400 mg, 2.5 mmol), followed by stirring the solution for 30 min. Piperidine (0.21 g, 2.5 mmol) was added, the resultant solution was further stirred for 1 h, and concentrated. The residue was partitioned between EtOAc and 1N HCl. The organic phase was washed with brine, dried (MgSO$_4$), and concentrated. The residue was purified by silica gel chromatography (100% EtOAc) to afford 720 mg (62%) of the title product.

$^1$H NMR (CDCl$_3$) δ: 8.32 (1H, br t, J=5.1), 7.32–7.10 (10H, m), 5.07 (2H, s), 5.01 (2H, s), 3.93 (1H, s), 3.55–3.05 (7H, m), 1.85–1.30 (10H, m);

High resolution FAB MS Calcd. for $C_{29}H_{36}H_5O_6$: (M+H) 550.2666. Found: 550.2656.

EXAMPLE 34 trans-4-(1-Piperidinocarbonyl)-3-[3-[N',N''-di(Cbz)-guanidino]-propyl]-1-acetyl-2-azetidin one (24)

To a −78° C. THF (10 mL) solution of 23 (334 mg, 0.61 mmol) was added 1N THF solution of sodium bis(trimethylsilyl)amide (0.65 mL, 0.65 mmol). The solution was stirred for 15 min, followed by the addition of acetyl chloride (47.4 mg, 0.6 mmol). The resultant reaction mixture was brought to room temperature and subsequently stirred for 30 min. The solution was concentrated, and the residue was partitioned between pH 4.0 aqueous buffer and EtOAc. The organic layer was dried (MgSO$_4$) and concentrated. The residue was purified by silica gel chromatography (3:1/Et$_2$O: EtOAc) to afford 155 mg (78%) of the title product.

$^1$H NMR δ: 8.33 (1H, br t, J=5.3) 7.36–7.18 (10H, m), 5.13 (2H, s), 5.04 (2H, s), 4.43 (1H, br s), 3.62–3.30 (6H, m), 3.28–3.18 (1H, m), 2.33 (3H, s), 1.85–1.30 (10H, m);

IR (film): 1795, 1735, 1720 cm$^{-1}$;

High resolution FAB MS Calcd. for $C_{31}H_{38}N_5O_7$: (M+H) 592.2771. Found: 592.2765.

EXAMPLE 35 trans-4-(1-Piperidinocarbonyl)-3-guanidinopropyl-1-acetyl-2-azetidinone hydrochloride salt (XI)

A methanolic (3 mL) solution of compound 24 (150 mg, 0.27 mmol) and 1N HCl (0.27 mL), containing 10% palladium on carbon, was stirred under a hydrogen atmosphere for 5 min. The suspension was filtered through a pad of Celite, and the filtrate was concentrated to afford 66 mg (68%) of the title compound.

$^1$H NMR (D$_2$O) δ: 4.93 (1H, br s), 3.76–3.22 (7H, m), 2.38 (3H, s), 1.97–1.23 (10H, m);

IR (film): 1795, 1710 cm$^{-1}$:

High resolution FAB MS Calcd. for $C_{15}H_{26}O_3N_5$: 324.2035. Found: 324.2030.

EXAMPLE 36 trans-4-(1-Piperidinocarbonyl)-3-[3-[N',N''-di(Cbz)guanidino]propyl]-1-[(5-dimethylamino)-1-naphthalenesulfonyl]-2-azetidinone (25)

To a −78° C. (12 mL) THF solution of compound 23 (640 mg, 1.16 mmol) was added 1N THF solution of sodium (1.25 mL, 1.25 mmol), followed by stirring the solution for 20 min. THF (20 mL) solution of dansyl chloride (320 mg, 1.17 mmol) was added. The resultant solution was brought to room temperature and stirred for 45 min. The solution was concentrated, and the residue was partitioned between ethyl acetate and pH 4.0 aqueous buffer. The organic phase was dried (MgSO$_4$) and concentrated. The crude product was purified by silica gel chromatography (100% Et$_2$O) to afford 380 mg (42%) of the title product.

$^1$H NMR (CDCl$_3$) δ: 8.57 (1H, d, J=7.1), 8.45 (1H, d, J=7.2), 8.26 (1H, d, J=6.0), 7.56 (1H, t, J=6.7), 7.51 (1H, t, J=6.7), 7.35–7.26 (10H, m), 7.15 (1H, d, J=6.3), 5.16 (2H, s), 5.09 (2H, s), 4.68 (1H, d, J=1.6), 3.55–3.27 (7H, m), 2.84 (6H, s), 1.87–1.35 (10H, m);

IR (KBr): 1800, 1737 cm$^{-1}$;

High resolution FAB MS Calcd. for $C_{41}H_{47}N_6O_8S_1$: (M+H) 783.3176. Found: 783.3162.

EXAMPLE 37 trans-4-(1-Piperidinocarbonyl)-3-guanidinopropyl-1-[(5-dimethylamino)-1-naphthalenesulfonyl]-2-azetidinone hydrochloride salt (XII).

A methanol/ethyl acetate (3 mL/1.5 mL) solution of compound 25 (360 mg, 0.48 mmol) and 1N HCl (0.55 mL), containing 10% palladium on carbon, was stirred under a hydrogen atmosphere for 10 min. The suspension was filtered through a pad of Celite, and the filtrate was concentrated to afford 196 mg (73%) of the title product.

$^1$H NMR (CD$_3$OD) δ: 8.82 (1H, br, d, J=7.0), 8.66 (1H, d. J=7.1), 8.36 (1H, d, J=6.1), 7.81-7.76 (3H, m), 5.07 (1H, d, J=2.1), 3.72-3.50 (3H, m), 3.42-3.06 (4H, m), 3.22 (6H, s), 1.92-1.43 (10H, m);

IR (KBr): 1800, 1735 cm$^{-1}$;

High resolution FAB MS Calcd. for C$_{25}$H$_{35}$N$_6$O$_4$: (M+H) 515.2441. Found: 515.2438.

EXAMPLE 38 trans-4-(1-Piperidinocarbonyl)-3-[3-[N',N''-di(Cbz)-guanidino]-propyl]-1-p-toluenesulfonyl-2-azetidinone (26)

To a −78° C. THF (10 mL) solution of compound 23 (379 mg, 0.69 mmol) was added 1N THF solution of sodium bis(trimethylsilyl)amide (0.7 mL), followed by stirring the solution for 20 min. p-Toluenesulfonyl chloride (131 mg, 0.69 mmol) was added, and the resultant solution was brought to room temperature. The solution was concentrated, and the residue was partitioned between ethyl acetate and pH 4.0 aqueous buffer. The organic phase was dried (MgSO$_4$) and concentrated. The residue was purified by silica gel chromatography to afford 160 mg (33%) of the title product.

$^1$H NMR (CDCl$_3$) δ: 7.87 (2H, d, J=8.4) 7.28 (2H, d, J=8.4), 7.40-7.22 (10H, m), 5.14 (2H, s), 5.07 (2H, s), 4.70 (1H, d, J=1.5 ), 3.54-3.32 (6H, m), 3.23-3.15 (1H, m), 2.37 (3H, s), 1.85-1.40 (10H, m);

IR (KBr): 1802, 1740 cm$^{-1}$;

High resolution FAB MS Calcd. for C$_{36}$H$_{42}$N$_5$O$_8$S: (M+H) 704.275. Found: 704.2767.

EXAMPLE 39 trans-4-(1-Piperidinocarbonyl)-3-guanidinopropyl-1-p-toluenesulfonyl-2-azetidinone hydrochloride salt (XIII)

An ethyl acetate/methanol (2.5 mL/2.5 mL) solution of compound 26 (157 mg, 0.22 mmol) and 1N HCl (0.22 mL), containing 10% palladium on carbon, was stirred under a hydrogen atmosphere for 10 minutes. The suspension was filtered through a pad of Celite and the filtrate was concentrated to afford 70 mg (67%) of the title compound.

$^1$H NMR (CD$_3$OD) δ: 7.86 (2H, d, J=8.3), 7.42 (2H, d, J=8.3), 5.06 (1H, d, J=2.6), 3.74-3.10 (7H, m), 2.44 (3H, s), 1.90-1.50 (10H, m);

IR (KBr): 1800, 1740 cm$^{-1}$;

High resolution FAB MS Calcd. for C$_{20}$H$_{30}$N$_5$O$_4$S: (M+H) 436.2018. Found: 436.2011.

EXAMPLE 40 trans-4-(2-Phenylethenyl)-3-[3-[N',N''-di(Cbz)guanidino]-propyl]-1-acetyl-2-azetidinone (27)

To a −78° C. THF (20 mL) solution of compound 3a (4.1 g, 7.64 mmol) was added 1N THF solution of sodium bis(trimethylsilyl)amide (7.64 mL), followed by stirring the solution for 15 min. Acetyl chloride (600 mg, 7.6 mmol) was added. The solution was warmed to room temperature, stirred for 75 min, and partitioned between ether and pH 4.0 aqueous buffer. The organic layer was dried (Na$_2$SO$_4$) and concentrated. The residue was purified by silica gel chromatography (Et$_2$O:-hexane/3:1) to afford 2.3 g (52%) of the title product.

$^1$H NMR (CDCl$_3$) δ: 8.36 (1H, br s), 7.43-7.20 (15H, m), 6.68 (1H, d, J=15.3), 6.20 (1H, dd, J=15.3, 7.7), 3.53-3.40 (2H, m), 3.10-3.0 (1H, m), 2.38 (3H, s), 1.90-1.65 (4H, m);

IR (film): 1780, 1735, 1710 cm$^{-1}$;

Anal. Calcd. for C$_{33}$H$_{34}$N$_4$O$_6$: C, 68.03; H, 5.88; N, 9.62. Found: C, 68.05; H, 5.99; N, 9.30.

High resolution FAB MS Calcd. for C$_{33}$H$_{35}$N$_4$O$_6$: (M+H) 583.2556. Found: 583.2543.

EXAMPLE 41 trans-4-Formyl-3-[3-[N',N''-di(Cbz)guanidino]propyl]-1-acetyl-2-azetidinone (28)

Ozone was passed through a −78° C. methylene chloride solution of compound 27 (0.7 g, 1.2 mmol) until a blue color was maintained. Excess ozone was removed by purging the solution with N$_2$. Dimethyl sulfide (1 mL) was added. The solution was warmed to room temperature, allowed to stand for 72 h, and concentrated. The residue was purified by silica gel chromatography (EtOAc:Et$_2$O/1:3) to afford 230 mg (38%) of the title product.

$^1$H NMR (CDCl$_3$) δ: 9.70 (1H, s ), 7.50-7.20 (10H, m), 5.17 (2H, s), 5.10 (2H, s), 4.17 (1H, br s), 3.56-3.30 (2H, m), 3.30-3.20 (1H, m), 2.40 (3H, s), 1.94-1.50 (4H, m);

IR (film): 1797, 1734, 1703 cm$^{-1}$;

High resolution FAB MS Calcd. for C$_{26}$H$_{29}$N$_4$O$_7$: (M+H) 509.2036. Found: 509.2031.

EXAMPLE 42 trans-4-Carboxy-3-[N',N''-di(Cbz)guanidino]propyl]-1-acetyl-2-azetidinone (29)

To an acetone solution of compound 28 (3.5 g, 6.8 mmol) was added freshly prepared Jones reagent dropwise until TLC indicated the disappearance of the starting material. The acetone layer was separated, and the residue was washed with a fresh portion of acetone. Two acetone portions were combined and concentrated. The residue was purified by silica gel chromatography (EtOAc:MeOH/99:1) to afford 2.4 g (66%) of the title product.

$^1$H NMR (CDCl$_3$) δ: 7.40-7.11 (10H, m), 5.17 (2H, s), 5.11 (2H, s), 4.13 (1H, d, J=2.3), 3.50-3.39 (2H, m), 3.26-3.17 (1H, m), 2.40 (3H, s), 1.96-1.65 (4H, m);

High resolution FAB MS Calcd. for C$_{26}$H$_{29}$N$_4$O$_8$: 525.1985. Found: 525.1991.

EXAMPLE 43 trans-4-Carboxy-3-guanidinopropyl-1-acetyl-2-azetidinone hydrochloride salt (XIV)

A methanol/ethyl acetate (3 mL/0.5 mL) solution of compound 29 (200 mg, 0.38 mmol) and 1N HCl (0.5 mL), containing 10% palladium on carbon, was stirred under a hydrogen atmosphere until TLC indicated the disappearance of the starting material (15 min). The suspension was filtered through a pad of Celite, and the filtrate was concentrated to afford 37 mg (33%) of the title compound.

$^1$H NMR (CD$_3$OD) δ: 4.18 (1H, d, J=3.3), 3.37-3.20 (3H, m), 2.35 (3H, s), 2.02-1.74 (4H, m);

IR (KBr): 1800, 1709 cm$^{-1}$;

High resolution FAB MS Calcd. for C$_{10}$H$_{19}$N$_4$O$_4$: (M+H) 257.1250. Found: 257.1244.

EXAMPLE 44 trans-4-(2-Phenylethyl)-3-guanidinopropyl-1-acetyl-2-azetidinone hydrochloride salt (XV)

A methanol/ethyl acetate (3 mL/1 mL) solution of compound 27 (470 mg, 0.82 mmol) and 1N HCl (0.9 mL), containing 10% palladium on carbon, was stirred under a hydrogen atmosphere until TLC indicated the disappearance of the starting material (about 30 min). The suspension was filtered through a pad of Celite, and the filtrate was concentrated to afford 220 mg (76%) of the title product.

$^1$H NMR (CD$_3$OD), selected peaks) δ: 7.5-7.10 (5H, m), 3.87-3.72 (1H, m), 2.30 (3H, s);

IR (film): 1770, 1710 cm$^{-1}$;

High resolution FAB MS Calcd. for C$_{17}$H$_{25}$N$_4$O$_2$: (M+H) 317.1977. Found: 317.1971.

EXAMPLE 45 trans-4-(4-Methylbenzeneaminocarbonyl)-3-[3-[N',N"-di(Cbz)guanidino]propyl]-1-acetyl-2-azetidinone (30)

To a −5° C. DMF (3.5 mL) solution of compound 29 (700 mg, 1.34 mmol) and p-toluidene (210 mg, 2 mmol) was added diphenylphosphoryl azide (550 mg, 2 mmol). The resulting solution was stirred for 30 min, subsequently warmed to room temperature, and stirred for an additional 1.5 h. The solution was partitioned between Et$_2$O and H$_2$O. The organic layer was dried (MgSO$_4$) and concentrated. The residue was chromatographed by silica gel chromatography (Et$_2$O:hexane/2:1) to afford 150 mg (18%) of the title product.

$^1$H NMR (CDCl$_3$) δ: 7.40-7.20 (10H, m), 7.24 (2H, d, J=8.4), 7.03 (2H, d, J=8.4), 5.17 (2H, s), 5.07 (2H, AB quartet), 4.43 (1H, d, J=2.3), 3.70-3.27 (3H, m), 2.42 (3H, s), 2.28 (3H, s), 2.0-1.62 (4H, m);

High resolution FAB MS Calcd. for C$_{33}$H$_{36}$N$_5$O$_7$: (M+H) 614.2615. Found: 614.2602.

EXAMPLE 46 trans-4-(4-Methylbenzeneaminocarbonyl)-3-guanidinopropyl-1-acetyl-2-azetidinone hydrochloride salt (XVI)

A methanol/ethyl acetate (2.0 mL/0.5 mL) solution of compound 30 (150 mg, 0.25 mmol) and 1N HCl (0.28 mL), containing 10% palladium on carbon, was stirred under a hydrogen atmosphere until TLC indicated the disappearance of the starting material (10 min). The suspension was filtered through a pad of Celite and the filtrate was concentrated to afford 70 mg (73%) of the title product.

$^1$H NMR (CD$_3$OD) δ: 7.45 (2H, d, J=7.2), 7.12 (2H, J=7.2), 4.32 (1H, d, J=3.2), 3.39-3.2 (3H, m), 2.37 (3H, s), 2.29 (3H, s), 1.91-1.59 (4H, m);

IR (KBr): 1802 cm$^{-1}$;

High resolution FAB MS Calcd. for C$_{17}$H$_{24}$N$_5$O$_3$: (M+H) 346.1879. Found: 346.1875.

EXAMPLE 47

6-[N',N"-Di(Cbz)guanidino]hexanoic acid (31)

A methanolic (350 mL) solution of N, N'-dicarbobenzyloxy-S-methyl-isothiourea (60 g, 0.18 mol), triethylamine (18.2 g, 0.18 mol), and 6-aminocaproic acid (23.3 g, 0.18 mol) was refluxed for 30 min and subsequently stirred at room temperature for 4 h. The solution was concentrated, and the residue was partitioned between ethyl acetate and water. The organic phase was separated, dried (MgSO$_4$), and concentrated. The residual solid was recrystallized from ethyl acetate/hexane to afford 52.3 g (66%) of the title product, mp 93° C.

$^1$H NMR (CDCl$_3$) δ: 7.43-7.20 (10H, m), 5.17 (2H, s), 5.10 (2H, s), 3.47-3.34 (2H, m), 2.33 (2H, d, J=6.9), 1.71-1.50 (4H, m), 1.45-1.30 (2H, m);

IR (KBr): 1740 cm$^{-1}$;

Anal. Calcd. for C$_{23}$H$_{27}$N$_3$O$_6$: C, 61.81; H, 5.89; N, 9.52 Found: C, 61.39; H, 6.29; N, 9.65.

EXAMPLE 48

6-[N',N"-Di(Cbz)guanidino]hexanoic acid methyl ester (32)

To a THF (300 mL) solution of compound 31 (50.8 g, 0.12 mol) was added carbonyldiimidazole (21.4 g, 0.132 mol). The resultant suspension was stirred for 1 h at room temperature. Methanol (75 mL) was added, followed by an additional stirring of the solution for 19 h. The solution was concentrated, and the residue was partitioned between water and ether. The organic phase was dried (MgSO$_4$) and concentrated. The residue was purified by silica gel chromatography (Et$_2$O:hexane/1:1) to afford 22.8 g (42%) of the title compound.

$^1$H NMR (CDCl$_3$) δ: 7.42-7.20 (10H, m), 5.16 (2H, s), 5.12 (2H, s), 3.64 (3H, s), 3.38 (2H, q, J=6.1), 2.27 (2H, t, J=6.9), 1.68-1.50 (4H, m), 1.42-1.28 (2H, m);

IR (film): 1740 cm$^{-1}$;

Anal. Calcd. for C$_{24}$H$_{29}$N$_3$O$_6$: C, 63.28; H, 6.42; N, 9.23. Found: C, 63.30; H, 6.51; N, 9.26.

EXAMPLE 49 trans-4-(2-Phenylethenyl)-3-[4-[N',N"-di(Cbz)guanidino]butyl]-2-azetidinone (33)

To a −40° C. THF (15 mL) solution of hexamethyldisilazane was added 2.5M THF solution of n-BuLi (60 mL, 0.15 mol). The resultant solution was stirred at −40° C. for 1 h and cooled to −78° C. A THF (30 mL) solution of compound 32 (22.2 g, 0.05 mol) was added, followed by stirring the solution for 1 h. The reaction mixture was warmed to −30° C. and stirred for 1 h. The solution was subsequently cooled to −78° C. A THF (30 mL) solution of N-(trimethylsilyl)benzaldimine (10.2 g, 0.05 mol) was added, followed by warming the solution to −30° C. and stirring for 30 min. The solution was warmed to −20° C. and allowed to stand at this temperature for 16 h. The resultant dark reaction mixture was concentrated to half of its original volume and partitioned between ether and 1N HCl; enough acid was used to eventually maintain the pH of the aqueous phase below 2.0. The organic phase was washed with water and brine, dried (MgSO$_4$), and concentrated. The residue was purified by silica gel chromatography (Et$_2$O:ETOAc/9:1) to afford 6.8 g (36%) of the title product.

$^1$H NMR (CDCl$_3$) δ: 7.43–7.20 (15H, m), 6.58 (1H, d, J=15.3), 6.18 (1H, dd, J=15.3, 8.4), 5.17 (2H, s), 5.10 (2H, s), 3.93 (1H, d, J=8.4, 2.0), 3.48–3.37 (2H, q, J=6.6), 2.95 (1H, br t, J=6.6), 1.92–1.40 (6H, m);

IR (KBr): 1760, 17333 cm$^{-1}$;

High resolution FAB MS Calcd. for C$_{32}$H$_{35}$N$_4$O$_5$: (M+H) 555.2607. Found: 555.259.

EXAMPLE 50 trans-4-(2-Phenylethenyl)-3-[4-[N′,N″-di(Cbz)-guanidino]butyl]-1-t-butyldimethylsilyl-2-azetidinone (34)

To a 0° C. DMF (25 mL) solution of compound 33 (6.8 g, 12.3 mmol) was added triethylamine (2.05 g, 20 mmol) and tert-butyldimethylsilyl chloride (3.05 g, 20 mmol). The reaction mixture was warmed to room temperature and stirred for 1.5 h. The suspension was partitioned between Et$_2$O and pH 7.0 aqueous buffer. The organic layer was dried (MgSO$_4$) and concentrated. The residue was purified by silica gel chromatography to afford 8.4 g (quantitative) of the title product.

$^1$H NMR (CDCl$_3$) δ: 7.40–7.15 (15H, m), 6.52 (1H, d, J=16.8), 6.1 (1H, d, J=16.8, 8.4), 5.1 (2H, s), 5.05 (2H, s), 3.77 (1H, d, J=8.4, 2.0), 3.37 (2H, q, J=6.1), 2.95–2.87 (1H, m), 1.85–1.35 (6H, m), 0.9 (9H, s), 0.2 (3H, s), 0.1 (3H, s);

IR (film): 1735 cm$^{-1}$;

High resolution FAB MS Calcd. for C$_{38}$H$_{49}$N$_4$O$_5$Si: (M+H) 669.3472. Found: 669.3466.

EXAMPLE 51

Step A trans-4-Formyl-3-[4-[N′,N″-di(Cbz)quanidino]butyl]-1-t-butyldimethylsilyl-2-azetidinone (35)

Ozone was passed through a −78° C. methylene chloride (100 mL) solution of compound 34 (8.2 g, 12 mmol) until the solution retained a blue color. Dimethyl sulfide (10 mL) was added. The solution was warmed to room temperature and allowed to stand for 16 h. The solution was concentrated to afford the title product which was not purified but used directly in Step B.

Step B trans-1-Methylcarbonyl-3-[4-[N′,N″-di(Cbz)quanidino]-butyl]-2-azetidinone (36)

The aldehyde prepared in Step A was dissolved in acetone (100 mL). To the resultant solution was added Jones reagent until TLC indicated the disappearance of starting material. The resultant solution was stirred for 2 h, concentrated to one third of its original volume, and partitioned between ethyl acetate and water. The organic layer was separated, dried (MgSO$_4$), and concentrated. The residue was eluted through silica gel with ethyl acetate: acetic acid (99:1) to afford 0.6 g of dark oil which was dissolved in methylene chloride. An ether solution of diazomethane was added dropwise until yellow color persisted. Excess diazomethane was decomposed with acetic acid. The solution was concentrated. The residue was purified by silica gel chromatography (Et$_2$O) to afford 250 mg (24% overall from compound 36) of the title product.

$^1$H NMR (CDCl$_3$) δ: 7.38–7.20 (10H, m), 5.13 (2H, s ), 5.07 (2H, s), 3.38 (2H, q, J=6.1), 3.17 (1H, br t, J=9.0), 1.89–1.37 (6H, m);

High resolution FAB MS Calcd. for C$_{26}$H$_{31}$N$_4$O$_7$: (M+H) 511.2193. Found: 511.2182.

EXAMPLE 52 trans-4-Methoxycarbonyl-3-[4-[N′,N″-di(Cbz-)guanidino]butyl]-1-[(5-dimethylamino)-1-naphthalenesulfonyl]-2-azetidinone (37)

To a −78° C. THF (3 mL) solution of compound 36 (250 mg, 0.49 mmol) was added 1N THF solution of sodium bis(trimethylsilyl)amide (0.55 mL). The resultant solution was stirred for 20 min. A THF (1 mL) solution of dansyl chloride ( 0.135 g, 0.5 mmol) was added. The resultant solution was allowed to warm to room temperature and concentrated. The residue was partitioned between ethyl acetate and aqueous pH 7.0 buffer. The organic layer was dried (MgSO$_4$) and concentrated. The residue was purified by silica gel chromatography to afford 141 mg (39%) of the title product.

$^1$H NMR (CDCl$_3$) δ: 8.59 (1H, d, J=8.5), 8.47 (1H, d, J=8.7), 8.27 (1H, d, J=6.2), 7.60 (1H, t, J=7.6), 7.53 (1H, t, J=7.5), 7.37–7.17 (11H, m), 5.15 (2H, s), 5.09 (2H, s), 4.21 (1H, d, J=3.1), 3.45 (3H, s), 3.34–3.22 (3H, m), 2.85 (6H, s), 1.81–1.36 (6H, m);

FAB MS: 744 (M+H).

EXAMPLE 53 trans-4-Methoxycarbonyl-3-(4-guanidinobutyl)-1-[(5-dimethyl amino)-1-naphthalenesulfonyl]-2-azetidinone hydrochloride salt (XVII)

A methanol/ethyl acetate (3 mL/1 mL) of compound 37 (130 mg, 0.18 mmol) and 1N HCl, containing 10% palladium on carbon, was stirred under a hydrogen atmosphere for 16 h. The suspension was filtered through a pad of Celite, and the filtrate was concentrated to afford 45 mg (50%) of the title product.

$^1$H NMR (CD$_3$OD) δ: 8.99 (1H, d, J=8.5), 8.86 (1H, d, J=8.2), 8.43 (1H, d, J=7.1), 8.10 (1H, d, J =6.9), 7.94–7.89 (2H, m), 4.52 (1H, s), 3.49 (3H, s), 3.44 (6H, s), 3.33–3.03 (3H, m), 1.88–1.20 (6H, m);

IR (film): 1807, 1753 cm$^{-1}$;

High resolution FAB MS Calcd. for C$_{22}$H$_{30}$N$_5$O$_5$S: (M+H) 467.1968. Found: 476.1978.

EXAMPLE 54 trans-4-[[2-[(Phenylmethoxy)carbonyl]-1-pyrrolidinyl]-
carbonyl]-3-[3-[N',N''-di(Cbz)
guanidino]propyl]-1-acetyl-2-azetidinone (38)

To a −5° C. methylene chloride (1 mL) solution of ethyl chloroformate (0.12 g, 1.1 mmol) was added a methylene chloride solution of compound 29 (0.35 g, 0.7 mmol), followed by the addition of triethylamine (0.112 g, 1.1 mmol). The resultant reaction mixture was stirred for 1 h between −5° C. and 5° C. Triethylamine (0.11 g, 1.1 mmol) and proline benzylester hydrochloride (260 mg, 1.1 mmol) was added, and the solution was stirred between −5° C. to 5° C. for an additional 15 min and for 16 h at room temperature. The solution was washed with saturated aqueous $NaHCO_3$ solution, dried ($MgSO_4$), and concentrated. The residue was purified by silica gel chromatography ($Et_2O$:EtOAc/8:2) to afford 70 mg (14%) of the title compound.

$^1$H NMR ($CDCl_3$) δ: 7.40–7.13 (15 H, m), 5.18–5.03 (6 H, m), 4.60–4.43 (½ H, m), 4.26–4.20 (½ H, m), 3.92–3.17 (6 H, m), 2.34 (3/2 H, s), 2.29 (3/2 H, s), 2.24–1.50 (8 H, m);

High resolution FAB MS Calcd. for $C_{38}H_{42}N_5O_9$: (M+H) 712.2990. Found: 712.2982.

EXAMPLE 55 trans-4-[(2-Carboxy-1-pyrrolidinyl)carbonyl]-3-(3-
guanidino)propyl-1-acetyl-2-azetidinone hydrochloride
salt (XVIII)

A methanol/ethyl acetate solution of compound 38 (150 mg, 0.2 mmol) and 1N HCl, containing 10% palladium on carbon, was stirred under a hydrogen atmosphere for 1.5 h. The suspension was filtered through a pad of Celite, and the filtrate was concentrated to afford 47 mg (60%) of the title product.

$^1$H NMR ($CD_3OD$) δ: 4.59 (¼ H, d, J=2.9), 4.52–4.49 (¼H, m), 4.45–4.40 (¼ H, m), 4.33 (¼ H, d, J=2.7 ), 4.04–3.92 (½ H, m), 3.58–3.50 (½ H, m) 3.42–3.15 (5H, m), 2.33 (3/2 H, s), 2.32 (3/2 H, s), 2.13–1.63 (8H, m);

IR (KBr): 1800, 1712 cm$^{-1}$.

EXAMPLE 56 trans-4-[[[2-Oxo-2-(phenylmethoxy)ethyl]amino]car-
bonyl]-3-[3-[N',N''-di(Cbz)guanidino]propyl]-1-acetyl-
2-azetidinone (39)

To a −10° C. methylene chloride (2 mL) solution of ethyl chloroformate (57 mg, 0.53 mmol) was added a methylene chloride (2 mL) solution of compound 29 (220 mg, 0.44 mmol) and triethylamine (530 mg, 0.13 mmol). The resultant solution was stirred between −5° C. and 5° C. for 1 h. Glycine benzyl ester hydrochloride (0.11 g, 0.64 mmol) was added, followed by triethylamine (0.53 g, 0.13 mmol). The resulting suspension was stirred at room temperature for 21 h and filtered through a sintered glass funnel. The solid was washed with methylene chloride. The filtrate and the washing portion were combined and washed with 1N HCl, dried ($MgSO_4$), and concentrated. The residue was purified by silica gel chromatography ($Et_2O$:EtOAc/9:1) to afford 140 mg (47%) of the title product.

$^1$H NMR ($CD_3OD$) δ: 7.43–7.18 (15H, m), 5.30–5.00 (6H, m), 4.26 (1H, d, J=3.2), 4.13 (1H, dd, J=18.1, 6.6), 3.82–3.63 (1H, m), 3.57 (1H, dd, J=18.1, 4.8), 3.38–3.28 (1H, m), 3.27–3.17 (1H, m), 2.39 (3H, s), 2.0–1.5 (4H, m);

IR (film): 1798, 1738, 1715 cm$^{-1}$.

EXAMPLE 57

4-[[(2-Hydroxy-2-oxoethyl)amino]carbonyl]-3-(3-
guanidinopropyl)-1-acetyl-2-azetidinone hydrochloride
salt (XIX)

A methanol/ethyl acetate solution of compound 41 (240 mg, 0.36 mmol) and 1N HCl (0.4 mL), containing 10% palladium on carbon, was stirred under a hydrogen atmosphere for 1 h. The suspension was filtered through a pad of Celite, and the filtrate was concentrated to afford 55 mg (44%) of the title product.

$^1$H NMR ($CD_3OD$) δ: 4.24 (1H, d, J=3.3), 4.08–3.85 (2H, m), 3.38–3.13 (3H, m), 2.35 (3H, s), 1.97–1.58 (4H, m);

IR (KBr): 1802, 1758, 1720, 1670 cm$^{-1}$;

High resolution FAB MS Calcd. for $C_{12}H_{20}N_5O_5$: (M+H) 314.1469. Found: 314.1460.

EXAMPLE 58

4-Acetyloxy-3-[3-[N',N''-di(Cbz)guanidino]propyl]-1-
acetyl-2-azetidinone (40)

To a −78° C. THF (20 mL) solution of compound 13 (trans:cis ratio, 2:1; 580 mg; 1.16 mmol) was added 1N THF solution of sodium bis(trimethylsilyl)amide (1.36 mL, 1.36 mmol), followed by 10 min stirring of the resultant solution. Acetyl chloride (96 mL, 1.36 mmol) was added, and the temperature of the resultant solution was raised to room temperature, stirred for 30 min, and concentrated. The residue was partitioned between ether and water. The organic phase was dried ($Na_2SO_4$) and concentrated. The residue was purified by silica gel chromatography (4:1/ether:hexane) to afford 420 mg (57%) of the product as a mixture of trans and cis (2:1) isomers.

$^1$H NMR ($CDCl_3$) δ: 7.42–7.20 (10H, m), 6.82 (⅓ H, d, J=5.4), 6.04 (⅔ H, d, J=1.5), 5.14 (2H, s), 5.08 (2H, s), 3.52–3.40 (2H, m), 3.17–3.07 (1H, m), 2.36 (2H, s), 2.32 (1H, s), 2.08 (2H, s), 2.05 (1H, s), 1.90–1.57 (4H, m);

IR (film): 1803, 1758, 1723 cm$^{-1}$;

High resolution FAB MS Calcd. for $C_{11}H_{20}N_4O_4$: (M+H) 271.1406. Found: 271.1404.

EXAMPLE 59

4-Acetyloxy-3-guanidinopropyl-1-acetyl-2-azetidinone
hydrochloride salt (XX)

A methanol/ethyl acetate (1:1/5 mL:5 mL) solution of compound 40 (420 mg, 0.78 mmol) and 1N HCl (0.76 mL), containing 10% palladium on carbon, was shaken in a Parr hydrogenator at 45 psi hydrogen pressure for 2 h. The suspension was filtered through a pad of Celite, and the filtrate was concentrated to afford 170 mg (71%) of the title product as a mixture of trans and cis (2:1) isomers.

$^1$H NMR ($CD_3OD$) δ: 6.55 (⅓ H, d, J=5.0), 6.11 (⅔ H, d, J=1.7), 3.34–3.13 (3H, m), 2.33 (2H, s), 2.31 (1H, s), 2.11 (1H, s), 2.09 (2H, s), 1.95–1.63 (4H, m);

IR (film): 1805, 1760, 1720 cm$^{-1}$;

EXAMPLE 60

4-Acetyloxy-3-[3-[N',N"-di(Cbz)guanidino]propyl]-1-t-butylcarbonyl-2-azetidinone (41)

To a −78° C. THF (6 mL) solution of compound 13 (trans:cis ratio, 2:1; 600 mg; 1.2 mmol) was added 1N THF solution of sodium bis(trimethylsilyl)amide (1.2 mL, 1.2 mmol), and the resultant solution was stirred for 15 min. Pivaloyl chloride (150 mg, 1.24 mmol) was added, and the solution was stirred for 30 min at −78° C. and for 1.5 h at room temperature. The reaction mixture was partitioned between pH 4.0 aqueous buffer and ether. The organic phase was dried (MgSO$_4$) and concentrated. The residue was purified by silica gel chromatography (1:1/Et$_2$O:hexane) to afford 300 mg (43%) of the title product as a mixture of trans and cis (3:2) isomers.

$^1$H NMR (CDCl$_3$) δ: 7.41–7.20 (10H, m), 6.53 (2.5 H, d, J=5.3), 6.07 (3/5, d, J=1.5), 5.14 (2H, s), 5.08 (2H, s), 3.47–3.38 (2H, m), 3.03–2.97 (1H, m), 2.06 (1.8 H, s), 2.04 (1.2 H, s), 1.84–1.60 (4H, m), 1.28 (5.4 H, s), 1.26 (3.6 H, s);

IR (film): 1802, 1734, 1703 cm$^{-1}$;

High resolution FAB MS Calcd. for C$_{30}$H$_{37}$N$_4$O$_8$: 581.2611. Found: 581.2603.

EXAMPLE 61

4-Acetyloxy-3-guanidinopropyl-1-t-butylcarbonyl-2-azetidinone hydrochloride salt (XXI)

A methanol/ethyl acetate solution of compound 41 (300 mg, 0.5 mmol) and 1N HCl (0.52 mL), containing 10% palladium on carbon, was stirred under a hydrogen atmosphere for 30 min. The suspension was filtered through a pad of Celite, and the filtrate was concentrated to afford 0.1 g (64%) of the title product as a mixture of trans and cis (3:2) isomers.

$^1$H NMR (CD$_3$OD) δ: 6.56 (2/5 H, d, J=5.1), 6.11 (3/5 H, d, J=1.6), 3.35–3.10 (3H, m), 2.10 (1.2H, s), 2.08 (1.8H, s), 1.97–1.52 (4H, m), 1.27 (5.4H, s), 1.26 (3.6H, s);

IR (KBr): 1804, 1751, 1705 cm$^{-1}$;

High resolution FAB MS Calcd. for C$_{14}$H$_{25}$N$_4$O$_4$: (M+H) 313.1876. Found: 313.1872.

EXAMPLE 62

4-Acetyloxy-3-[3-[N',N"-di(Cbz)guanidino]propyl]-1-phenylcarbonyl-2-azetidinone (42)

To a −78° C. THF (4 mL) of compound 13 (500 mg, 1 mmol) was added 1N THF solution of sodium bis(trimethylsilyl)amide (1.0 mL, 1.0 mmol), and the resultant reaction mixture was stirred for 15 min. Benzoyl chloride (140 mg, 1 mmol) was added, and the mixture was stirred for 30 min at −78° C. and for 90 min at room temperature. The solution was subsequently partitioned between ether and aqueous pH 4.0 buffer. The organic layer was dried (MgSO$_4$) and concentrated. The residue was purified by silica gel chromatography (Et$_2$O:hexane/2:1) to afford 200 mg (33%) of the title product as a mixture of trans and cis (3:1) isomers.

$^1$H NMR (CDCl$_3$) δ: 7.63–7.16 (15H, m), 6.75 (¼ H, d, J=5.1), 6.30 (¾, d, J=1.9), 5.15 (2H, s), 5.10 (2H, s), 3.56–3.35 (2H, m), 3.30–3.16 (1H, m), 2.11 (2.25 H, s), 2.09 (0.75 H, s), 1.93–1.63 (4H, m);

IR (film): 1866, 1749 cm$^{-1}$;

High resolution FAB MS Calcd. for C$_{32}$H$_{33}$N$_4$O$_8$: (M+H) 601.2298. Found: 601.2290.

EXAMPLE 63

4-Acetyloxy-3-guanidinopropyl-1-phenylcarbonyl-2-azetidinone hydrochloride salt (XXII)

A methanol/ethyl acetate solution of compound 44 (200 mg, 0.33 mmol) and 1N HCl (0.33 mL), containing 10% palladium on carbon, was stirred under a hydrogen atmosphere for 30 min. The suspension was filtered through a pad of Celite, and the filtrate was concentrated to afford 100 mg (82%) of the title product as a mixture of trans and cis (3:1) isomers.

$^1$H NMR (CD$_3$OD) δ: 7.68–7.42 (5H, m), 6.76 (¼ H, d, J=5.2), 6.32 (¾ H, d, J=1.9), 3.44–3.10 (3H, m), 2.14 (0.75H, s, 2.14), ¾ 2.12 (2.25H, s), 2.06–1.58 (4H, m);

IR (film): 1806, 1749 cm$^{-1}$;

High resolution FAB MS Calcd. for C$_{16}$H$_{21}$N$_4$O$_4$: (M+H) 333.1563. Found: 333.1565.

EXAMPLE 64 cis-4-(1-Piperidinocarbonyl)-3-[3-[N',N"-di(Cbz)-guanidino]propyl]-2-azetidinone (43)

To a THF (12 mL) solution of compound 6b (1.3 g, 2.7 mmol) was added carbonyldiimidazole (0.53 g, 3.24 mmol), and the resultant solution was stirred for 35 min. Piperidine (230 mg, 2.7 mmol) was added, and the reaction mixture was stirred for an additional hour and concentrated. The residue was partitioned between EtOAc and 0.5N HCl. The organic phase was dried (MgSO$_4$) and concentrated. The residue was purified by silica gel chromatography to afford 360 mg (24%) of the title compound;

$^1$H NMR (CDCl$_3$) δ: 7.38–7.18 (10H, m), 5.12 (2H, s), 5.03 (2H, s), 4.33 (1H, d, J=5.4), 3.52–3.02 (7H, m), 1.90–1.40 (10H, m).

EXAMPLE 65 cis-4-(1-Piperidinocarbonyl)-3-[3-[N',N"-di(Cbz)-guanidino]propyl]-1-acetyl-2-azetidinone (44)

To a −78° C. THF (2 mL) solution of compound 43 (360 mg, 0.65 mmol) was added 1N THF solution of sodium bis(trimethylsilyl)amide (0.65 mL), and the resultant solution was stirred for 20 min. Acetyl chloride (0.05 mL, 0.7 mmol) was added, and the solution was warmed to room temperature and stirred for an additional hour. The solution was partitioned between ether/ethyl acetate and pH 4.0 aqueous buffer solution. The organic phase was dried (MgSO$_4$) and concentrated. The residue was purified by silica gel chromatography (100% EtOAc) to afford 240 mg (62%) of the title product.

$^1$H NMR (CDCl$_3$) δ: 7.40–7.20 (10H, m), 5.13 (2H, s), 5.06 (2H, s), 6.76 (1H, d, J=6.1), 3.58–3.12 (7H, m), 2.36 (3H, s), 1.86–1.34 (10H, m);

IR (KBr): 1798, 1740, 1722 cm$^{-1}$;

High resolution FAB MS Calcd. for C$_{31}$H$_{38}$N$_5$O$_7$: (M+H) 592.2711. Found: 592.2769.

EXAMPLE 66 cis-4-(1-Piperidinocarbonyl)-3-guanidinopropyl-1-acetyl-2-azetidinone hydrochloride salt (XXIII)

A methanol (2 mL) solution of compound 46 (240 mg, 0.4 mmol) and 1N HCl (0.5 mL), containing 10% palladium on carbon, was stirred under a hydrogen atmosphere for 15 min. The suspension was filtered through a pad of Celite, and the filtrate was concentrated to afford 124 mg (86%) of the title product.

$^1$H NMR (CD$_3$OD) δ: 5.04 (1H, d, J=6.7), 3.83–3.17 (7H, m), 2.34 (3H, s), 192–1.50 (10H, m);

IR (film): 1798, 1715 cm$^{-1}$:

High resolution FAB MS Calcd. for C$_{15}$H$_{26}$N$_5$O$_3$: (M+H) 324.2035. Found: 324.2032.

EXAMPLE 67

N-(trimethylsilyl)cinnamilydenimine

A procedure analogous to that reported by C. Kruger et al. [*Chem. Ber.* 96, 2132 (1963)] was employed. To a −78° C. THF (1600 ml) solution of 1,1,1,3,3,3-hexamethyldisilazane (221.9 g, 137 mol) was added 2.5M hexane solution of n-butyllithium (550 mL, 1.38 mole). The resultant solution was stirred for 30 min. A THF (200 mL) solution of cinnamaldehyde (165.2 g, 1.25 mole) was added dropwise, and the solution was stirred for another 30 min. Trimethylchlorosilane (149.4 g, 1.38 mol) was added, and the solution was allowed to warm up to room temperature and stirred for 2 h. The suspension was concentrated. The residue was triturated with anhydrous ether, and the solid was separated by passing the suspension through a pad of Celite. The filtrate was concentrated, and the residue was distilled under reduced pressure to afford 190 g (68%) of the title product, b.p. 85° C. (0.15 mmHg).

$^1$H NMR (CDCl$_3$) δ: 8.56 (1H, d, J=7.6), 7.38–7.03 (5H, m), 6.94 (1H, d, J=16.1), 6.68 (1H, dd, J=16.1, 7.6), 0.11 (9H,S), 0.08(3H, S), 0.01 (3H, s).

EXAMPLE 68

Biological Testing

1. Enzyme Assays for the Inhibition of Thrombin

The following reagents were used in these assays:

Thrombin assay buffer: 145 mM NaCl, 5 mM KCl, 30 mM N-2-hydroxyethyl piperazine-N'-2-ethanesulfonic acid, pH 7.4, 1 mg/ml polyethylene glycol (PEG-8000).

3 mM D-Phe-Pip-Arg-p-nitroanilide (s-2238) in H$_2$O.

3 U/ml purified human α-thrombin dissolved in thrombin assay buffer.

Inhibitors to be tested were dissolved in H$_2$O, methanol, or DMSO just prior to use.

Assay Procedure

To each well in a 96-well microtiter plate, 270 μl of assay buffer was added. Human α-thrombin (10 μl of 3 U/ml) was added, then 10 μl of inhibitor were added and mixed. The samples were incubated at room temperature for a defined period of time (3 min for initial IC$_{50}$ determinations). The enzymic reaction was started with 10 μl of 3 mM s-2238 substrate and continued at room temperature. The change in optical density was measured at 405 nm. A kinetic microplate reader (Molecular Devices Corporation V$_{max}$) was used to measure the change in optical density over time.

Results are reported in Table 1 as IC$_{50}$ values, i.e., the drug concentration in mole/liter which caused 50% inhibition of the enzyme activity (after incubation of the drug with the enzyme for 3 min).

Alternatively, results are also reported in Table 1 expressed as $k_2/k_i$ which is the second order rate constant in per mole per minute for inactivation time of the enzyme [Kitz, et al., J. Biol. Chem., 237, 3245 (1962)].

2. Enzyme Assays for the Inhibition of Trypsin

The following reagents were used in these assays:

Trypsin assay buffer: 2 mM CaCl$_2$, 50 mM Tris/Cl pH 8.0.

3 mM Z-Val-Gly-Arg-pNA (Chromzyme TRY) dissolved in H$_2$O.

6 μg/ml of purified bovine pancreatic trypsin dissolved in trypsin assay buffer.

Inhibitors to be tested were dissolved in H$_2$O, methanol or DMSO just prior to use.

Assay Procedure

To each well in a 96-well microtiter plate, 270 μl of assay buffer was added. Bovine trypsin (10 μl of 6 μg/ml) was added. Inhibitor (10 μl) was added, mixed, and then incubated at room temperature for 3 min. The enzymic reaction was started with 10 μl of 3 mM Z-Val-Gly-Arg-pNA substrate. The change in optical density was measured at 405 nm at room temperature. A kinetic microplate reader (Molecular Devices Corporation V$_{max}$) was used to measure the change in optical density over time.

Results are reported in Table 1 as IC$_{50}$ values, i.e., the drug concentration in mole/liter which caused 50% inhibition of the enzyme activity (after incubation of the drug with the enzyme for 3 min).

Procedure for Determining the Concentration Required for Doubling Thrombin Clotting Time—Clotting Time Assays The following reagents were used in these assays:

Owren's Veronal Buffer: 125 mM NaCl, 28.4 mM sodium barbital, pH 7.35.

Human citrated plasma obtained from human volunteers or citrated plasma obtained from IP-dosed animals (prepared as described below).

25 NIH Units/ml human α-thrombin in thrombin buffer for use with rat plasma.

10 NIH Units/ml human α-thrombin in thrombin buffer for use with human plasma.

Preparation of the Citrated Plasma

Human Plasma: Blood from human volunteers was drawn into vacutainer tubes containing one tenth final volume of 0.129M (3.8%) buffered citrate (16 mg Na$_3$-Citrate.2H$_2$O and 2.1 mg citric acid per milliliter of H$_2$O). The blood was centrifuged at 3500 rpm (480 x g) for 15 min at room temperature (using a Sorvall RT 6000B centrifuge). The plasma was removed, pooled, and aliquoted into small tubes which were stored frozen for later use.

Dosing: Test compound was prepared just prior to dosing. Routinely the drugs are dissolved in water. Animals were dosed by i.p. injection.

Blood Drawing for Rats: After the appropriate time period, the animals were ether-anesthetized, and blood was drawn by cardiac puncture using 333 µl of 3.8% sodium citrate per 3 ml blood. After all of the samples were obtained, the tubes were centrifuged at 1,500 rpm for 15 min as described for the human blood samples.

Clotting Time Measurement

Clotting times were determined by pipetting 0.1 ml of Owren's buffer (pre-warmed 37° C.) and 0.1 ml of human or rat plasma into yellow sample cuvettes. For studies with human plasma 10 U/ml human thrombin (10 ml) was placed in the reservoir assembly station of the MLA 700. (Medical Laboratory Automation, Electra 700 Reservoir Assembly). For rat studies, the human thrombin concentration was 25 U/ml. The cuvettes were vortexed and then placed on the MLA 700 sample wheel. The coagulation timer (MLA 700) automatically dispenses 0.1 ml human thrombin into the sample in each cuvette. Detection of the fibrin clot was determined optically by the MLA 700.

Studies were performed to determine the concentration of drug which caused a doubling of the clotting time in human plasma. From standard curves of thrombin activity added to the sample versus the clotting time, the concentration of drug which caused a doubling of the thrombin clotting time corresponded to inhibition of approximately ½ of the added thrombin clotting activity. Results are reported in Table 1 as $ED_{50}$ values, i.e., the drug concentration required to double clotting time.

In separate studies, two compounds, Compound XIX and Compound XI, were dosed 50 mg/kg I.P. to three rats in each study group. Both compounds prolonged clotting time as measured ex vivo (by the method described above). Results of such study are presented in Table 2. "Term" indicates "terminated sample" where a clot was unable to form after approximately 99 seconds. When this occurred, the animal plasma was diluted 1:1 with control rat plasma and the sample tested again. If needed, the animal plasma was diluted 1:4 and tested again.

The foregoing biological results show that the compounds of the present invention exhibit anti-thrombin and anti-tripsin activities and are thus useful in controlling blood coagulation and treating pancreatitis.

TABLE 1

| Example Number | Compound Number | BIOLOGICAL ACTIVITIES | | | Trypsin |
|---|---|---|---|---|---|
| | | Thrombin | | | |
| | | $k_2/k_i$ (m$^{-1}$min$^{-1}$) | $IC_{50}$ (nM) | $ED_{50}$ (µM) | $IC_{50}$ (nM) |
| 10 | I | $1.2 \times 10^8$ | 2–9 | 65 | 8 |
| 12 | II | $1.9 \times 10^7$ | 2 | 1.25 | 40 |
| 14 | III | $2.1 \times 10^7$ | 16 | 50 | 720 |
| 16 | IV | $1.5 \times 10^6$ | 20 | NT | 70 |
| 18 | V | $8.3 \times 10^4$ | 1700 | 30 | 5.0 |
| 22 | VI | $3.0 \times 10^6$ | 3.2 | 15 | 750 |
| 25 | VII | $5.6 \times 10^6$ | 12.5 | 0.75 | 36 |
| 28 | VIII | $2.5 \times 10^5$ | 100 | 4.0 | NT |
| 30 | IX | * | 1000 | 30 | NT |
| 32 | X | $3.0 \times 10^6$ | NT | NT | NT |
| 35 | XI | $4.2 \times 10^5$ | 90 | 0.5 | 9 |
| 37 | XII | $2.8 \times 10^6$ | 10 | 30 | 14 |
| 39 | XIII | $4.5 \times 10^7$ | 3 | 80 | 120 |
| 43 | XIV | | 390 | 12 | 12 |
| 44 | XV | $1.5 \times 10^6$ | 210 | 3 | 470 |
| 46 | XVI | $1.3 \times 10^6$ | 25 | 0.5 | 120 |
| 53 | XVII | $3.7 \times 10^5$ | | 50 | NT |
| 55 | XVIII | $4.3 \times 10^6$ | 49 | 1.25 | NT |
| 57 | XIX | $2.0 \times 10^7$ | 12 | 0.43 | NT |
| 59 | XX | $4.2 \times 10^7$ | 12 | 0.34 | 12 |
| 61 | XXI | $2.4 \times 10^6$ | 74 | 2.0 | NT |
| 63 | XXII | * | 35 | 10.0 | NT |
| 66 | XXIII | $4.3 \times 10^4$ | NT | 20 | NT |

*not measurable
NT = not tested

TABLE 2

| Animal | Condition | Thrombin Induced Clotting Time (Seconds) | Thrombin Induced Clotting Time (1:1 Control Plasma) | Thrombin Induced Clotting Time (1:4 Control Plasma) |
| --- | --- | --- | --- | --- |
| 1 | Control | 10.9 | | |
| 2 | No drug | 11.1 | | |
| 3 | | 10.9 | | |
| 4 | Compound XIX 0.5 hr. | term. | 14.4 | |
| 5 | post dose | 45.2 | | |
| 6 | | term. | 17.3 | |
| 7 | Compound XIX 2 hr. | 12.9 | | |
| 8 | post dose | 13.3 | | |
| 9 | | 14.4 | | |
| 10 | Compound XIX 5 hr. | 13.5 | | |
| 11 | post dose | 13.6 | | |
| 12 | | 13.3 | | |
| 13 | Compound XI 0.5 hr. | term. | term. | 18.0 |
| 14 | post dose | term. | term. | 17.7 |
| 15 | | term. | term. | 32.4 |
| 16 | Compound XI 2 hr. | term. | 45.7 | 14.0 |
| 17 | post dose | 17.2 | | |
| 18 | | 14.7 | | |
| 19 | Compound XI 5 hr. | 13.1 | | |
| 20 | post dose | 11.4 | | |
| 21 | | 11.5 | | |

What is claimed is:

1. A process for preparing compounds of Formulas 3a' and 3b'

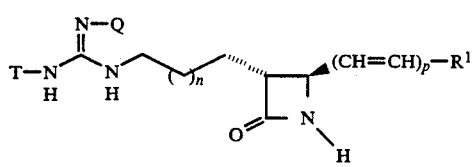

3a'

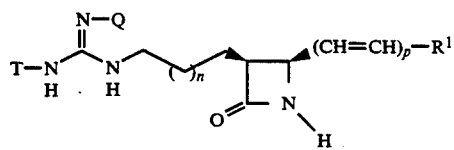

3b' wherein Q and T can be the same or different amino protecting groups, p is 1 or 2, $R^1$ is phenyl or alkyl substituted phenyl, n is 1 to 3; comprising the steps of:

(a) forming a trianion of a compound of Formula iv using a strong base

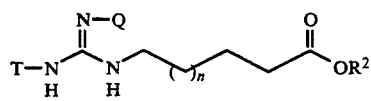

iv wherein T, Q and n are as defined above and $R^2$ refers to alkyl;

(b) reacting the trianion of a compound of Formula iv with a silylimine of Formula v

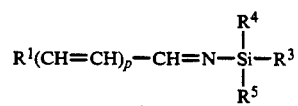

v wherein $R^1$ and p are as defined above and $R^3$, $R^4$ and $R^5$ can independently be alkyl, phenyl or alkyl substituted phenyl to afford a compound of Formula vi

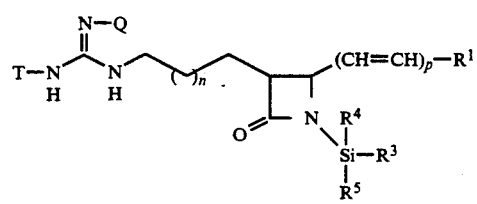

vi in which T, Q, n, p, $R^1$, $R^4$, $R^3$ and $R^5$ are as defined previously;

(c) hydrolyzing the nitrogen silicone bond of a compound of Formula vi to afford a compound of the formula 3, and

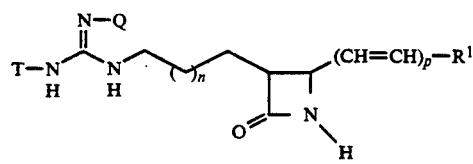

3

(d) separating the cis and trans isomers of a compound of Formula 3 to produce compounds of Formulas 3a' and 3b'.

2. The process of claim 1 in which T and Q are each independently t-butoxycarbonyl or phenylmethoxycarbonyl; n is 1 or 2; p is 1; $R^1$ is phenyl, $R^2$ is methyl; and $R^3$, $R^4$ and $R^5$ are methyl.

* * * * *